US006645150B2

(12) United States Patent
Angelsen et al.

(10) Patent No.: US 6,645,150 B2

(45) Date of Patent: Nov. 11, 2003

(54) WIDE OR MULTIPLE FREQUENCY BAND ULTRASOUND TRANSDUCER AND TRANSDUCER ARRAYS

(76) Inventors: Bjorn A. J. Angelsen, Bugges veg 4b, 7051 Trondheim (NO); Tonni F. Johansen, Osloveien 6, 7018 Trondheim (NO)

( * ) Notice: Subject to any disclaimer, the term of this patent is extended or adjusted under 35 U.S.C. 154(b) by 54 days.

(21) Appl. No.: 10/041,311

(22) Filed: Jan. 7, 2002

(65) Prior Publication Data

US 2002/0156379 A1 Oct. 24, 2002

Related U.S. Application Data

(60) Provisional application No. 60/260,023, filed on Jan. 5, 2001.

(51) Int. Cl.[7] .................................................. A61B 8/00

(52) U.S. Cl. .................................................. 600/459

(58) Field of Search ................................ 600/443, 447, 600/458, 459; 30/320–322, 334, 336, 345, 348

(56) References Cited

U.S. PATENT DOCUMENTS 4,096,756 A * 6/1978 Alphonse ..................... 73/609
4,345,139 A * 8/1982 Higgins ...................... 310/358
4,348,904 A * 9/1982 Bautista, Jr. ................. 73/644
4,482,835 A * 11/1984 Bar-Cohen et al. ......... 310/327
5,163,436 A * 11/1992 Saitoh et al. ............... 600/459
5,345,139 A * 9/1994 Gururaja et al. ............ 310/358
5,354,132 A * 10/1994 Young et al. ............... 310/334
5,410,205 A * 4/1995 Gururaja et al. ............ 310/328
5,457,353 A * 10/1995 Thurn et al. ................ 310/334
5,553,035 A * 9/1996 Seyed-Bolorforosh et al. .......................... 367/140
5,598,051 A * 1/1997 Frey ........................... 310/334
5,724,976 A * 3/1998 Mine et al. ................. 600/459
5,825,117 A * 10/1998 Ossmann et al. ........... 310/317
5,906,580 A * 5/1999 Kline-Schoder et al. .... 600/459
5,957,851 A * 9/1999 Hossack ...................... 600/459
6,107,722 A * 8/2000 Thurn ......................... 310/322
6,229,247 B1 * 5/2001 Bishop ....................... 310/328
6,416,478 B1 * 7/2002 Hossack ...................... 600/459
6,492,762 B1 * 12/2002 Pant et al. .................. 310/334

* cited by examiner

*Primary Examiner*—Francis J. Jaworski
(74) *Attorney, Agent, or Firm*—Cohen, Pontani, Lieberman & Pavane

(57) ABSTRACT

Ultrasound bulk wave transducers and bulk wave transducer arrays for wide band or multi frequency band operation, in which the bulk wave is radiated from a front surface and the transducer is mounted on a backing material with sufficiently high absorption that reflected waves in the backing material can be neglected. The transducer is formed of layers that include a high impedance section comprised of at least one piezoelectric layer covered with electrodes to form an electric port, and at least one additional elastic layer, with all of the layers of the high impedance section having substantially the same characteristic impedance to yield negligible reflection between the layers. The transducer further includes a load matching section comprised of a set of elastic layers for impedance matching between the high impedance section and the load material and, optionally, impedance matching layers between the high impedance section and the backing material for shaping the transducer frequency response. For multiband operation, the high impedance section includes multiple piezoelectric layers covered with electrodes to form multiple electric ports that can further be combined by electric parallel, anti-parallel, serial, or anti-serial galvanic coupling to form electric ports with selected frequency transfer functions. Each electric port may be separately transceiver-connected to obtain parallel, anti-parallel, serial or anti-serial port coupling for multi-band transmission, and extremely wide-band reception.

53 Claims, 25 Drawing Sheets

WIDE OR MULTIPLE FREQUENCY BAND ULTRASOUND TRANSDUCER AND TRANSDUCER ARRAYS

This application claims the benefit of Provisional Application No. 60/260,023, filed Jan. 5, 2001.

BACKGROUND OF THE INVENTION

1. Field of the Invention

The present invention is directed to technology and designs of efficient ultrasound bulk wave transducers for wide frequency band operation, and also transducers with multiple electric ports for efficient operation in multiple frequency bands, for example frequency bands with a harmonic relation, where it is possible to receive the $1^{st}$, and/or $2^{nd}$, and/or $3^{rd}$, and/or $4^{th}$ harmonic frequency bands of the transmitted frequency band.

2. Description of the Related Art

In medical ultrasound imaging, one uses a variety of center frequencies of the transmitted pulse to optimize image resolution for required image depth. To image deep organs one can use frequencies down to ~2 MHz, while for shallow depths one can use frequencies higher than 10 MHz.

In many cases one also transmits an ultrasound pulse in one band of frequencies, and receive the back scattered signal in a second band of frequencies. This is for example done in $2^{nd}$ harmonic imaging of tissue, where the receive band is centered around the $2^{nd}$ harmonic frequency of the transmit pulse band. Nonlinear elasticity in the tissue distorts the forward propagating pulse, which increases the higher harmonic content in the pulse with depth. This method considerably reduces noise in the ultrasound image.

Second harmonic imaging is also used for the detection of ultrasound contrast agent. As the nonlinear elasticity of the contrast agent is very strong, it is also interesting to use a receive band centered around higher than the $2^{nd}$ harmonic band, for example the $3^{rd}$ or $4^{th}$ harmonic component of the transmit frequency band.

It is also useful to transmit an ultrasound burst with two separate frequency bands, both for imaging of soft tissue and ultrasound contrast agents. The non-linear effects will then introduce new frequency bands in the scattered signal, centered around sums and differences of the transmitted center frequencies. When the center frequencies of the transmitted frequency bands coincide, the difference frequency is referred to as a sub harmonic frequency component produced by the non-linearity of the tissue or contrast agent elasticity.

Traditional ultrasound transducers for medical imaging have limitations for such applications in that they are efficient over a limited band of frequencies. The active material in the transducers, is usually a plate of piezoelectric ceramic that vibrates in thickness mode. Other piezoelectric materials like the crystal $LiNbO_3$, or the polymer PVDF, are also sometimes used. In the following we mainly refer to ceramic materials while it is understood that other piezoelectric materials can be used in the same manner.

The ceramic has much higher characteristic mechanical impedance ($Z_x$~34MRayl) than the tissue ($Z_x$~1.5MRayl), and the energy coupling between the tissue and the ceramic plate is therefore by nature very low. To improve this energy coupling, the plate is operated around $\lambda/2$ resonance when the backing mount has a lower characteristic impedance than the piezoelectric plate, or $\lambda/4$ resonance when the backing mount has a higher characteristic impedance than the piezoelectric plate. The resonance increases the amplitude of the thickness vibrations, hence improving the tissue/ceramic energy coupling at the resonance frequency. The resonance, however, gives a limited bandwidth of the energy coupling, limiting the minimal pulse length transmitted through the transducer.

To increase the bandwidth of the energy coupling, impedance matching layers are commonly used between the tissue and the ceramic plate to raise the mechanical impedance seen from the plate towards the tissue. Further improvement in the bandwidth of the tissue/ceramic energy coupling, is obtained with the well known ceramic/polymer composite materials. Such materials are made by dicing grooves in the ceramic plate and filling the grooves with softer polymer, a process that produces a composite ceramic/polymer material with mechanical impedance $Z_x$~12–20MRayl, substantially lower than for the whole ceramic.

Even with these techniques, it is difficult to produce efficient energy coupling bandwidths larger than ~80% of the center resonance frequency, limiting the bandwidth to ~35% for $2^{nd}$ harmonic imaging, and making it impossible to use higher than the $2^{nd}$ harmonic component of the back scattered signal for imaging. The reason for this is that the transducer plate is the dominant resonant layer in the structure, and the electrodes are placed on the surface of the piezoelectric layer so that the electrode distance becomes large at high frequencies.

For improved bandwidth with $2^{nd}$ harmonic imaging, there has been presented transducer structures with two piezoelectric layers with electrodes on the surfaces that gives a dual band performance. Through coupling of the electrodes one is able to transmit selectively in a low and a high frequency band, and receive selectively in the same low and high frequency bands. However, the presented patents make less than optimal use of the multilayer design for widest possible bandwidth, and the flexibility for selecting transduction in different frequency bands is limited.

The present invention presents a new layered transducer structure including optimized examples of the design that provides wider transduction bandwidths than previous designs, allowing transmission and reception of ultrasound pulses over two octaves, i.e. from a $1^{st}$ to a $4^{th}$ harmonic component of the lowest frequency band. The invention also provides details of efficient manufacturing of the layered structure. The method to increase the bandwidth is also useful for single piezoelectric layer transducers, increasing the relative bandwidth of such transducers to above 100%. This makes single piezoelectric layer transducer efficient for $2^{nd}$ harmonic imaging and also for $1^{st}$ harmonic imaging in different frequency bands.

The invention further presents methods for electronic selection of a wide variety of combinations of electro-acoustic ports in multi-layered transducers, for electronic selection of the efficient transduction bands of the transducer. This allows the transmit ultrasound pulses with frequency components in multiple bands, say both a $1^{st}$ and a $2^{nd}$ harmonic band, with transmitter amplifiers that switches the drive voltage between +V, −V, and zero. The invention further devices methods of combining the received signals from multiple electric ports for parallel reception of signals over two octaves of frequencies, or in a $1^{st}$, $2^{nd}$, $3^{rd}$, and even $4^{th}$ harmonic component of the transmitted frequency band.

SUMMARY OF THE INVENTION

The invention presents solutions to the general need for ultrasound transducers that can efficiently operate over a large frequency band, or in separated frequency bands both for transmit and receive, so that: 1) one can use the same transducer to operate with several ultrasound frequencies to select the optimal frequency for the actual depth, 2) one can obtain wider transmit and receive bands with $2^{nd}$ harmonic measurements and imaging, 3) one can receive higher than the $2^{nd}$ harmonic component of the transmitted pulse, for measurement and imaging of objects with high non-linear elastic properties, and 4) one can transmit a complex ultrasound burst containing frequencies in more than one frequency band, and receive signals in frequency bands centered around sums and differences of the transmitted center frequencies.

According to the present invention, such wide band or multi band operation of the transducer is achieved through three design attributes:

1. Overall structure: The total transducer is composed of a set of piezoelectric and purely elastic layers, mounted on a backing material with so high absorption that reflected waves in the backing material can be neglected. The layers are grouped into: 1) a core, high impedance section that contains the piezoelectric layers, 2) a load matching section of elastic impedance matching layers between the high impedance section and the load, and 3) possibly also a back matching section of elastic impedance matching layers between the high impedance section and the backing material.

The high impedance section is composed of piezoelectric and possibly also purely elastic layers, where all layers of this section have close to the same characteristic impedance $Z_x$, which is the highest value in the whole structure. As the exact value of the characteristic impedance is difficult to control and can vary even within a piezoelectric layer, the requirement of constant characteristic impedance within this section must be viewed as fuzzy and imprecise where up to a 20% variation can be tolerated, as discussed below. The basic requirement is that the high impedance section functions as a unity when determining resonances of the structure. The resonances of the structure is then determined by the total thickness $L_x$ of the whole high impedance section, and not by the thickness of the individual piezoelectric layers.

The highest sensitivity of the transducer is obtained by minimizing the power transmitted into the backing. This is obtained by either selecting the lowest or highest possible characteristic impedance of the backing material so that the velocity reflection coefficient at the backing interface is close to +1 or −1. Matching layers between the piezoelectric section and backing can be used to reduce the power transmitted into the backing in certain frequency ranges, for example to increase the sensitivity for high frequencies in a band. A problem with such matching is that its resonant nature can reduce the overall operating band of the transducer.

The load matching layers are according to well known methods selected to transform the load characteristic impedance to a higher value close to $Z_x$, over as large frequency range as possible. This is done with standard methods where one for example can choose equal ripple, or an exponential tapering, of the reflection coefficient between the high impedance section and the load matching section, with $\lambda/4$ layer thickness of the matching layers at the center of the efficient matching band. With such an arrangement of the layers, the reflection coefficient between the high impedance section and the load matching section can be made small over the effective frequency range of the impedance matching. The invention also devices a new method of manufacturing such layers as metal/polymer composites similar to the high impedance elastic layers described below.

When the impedance seen from the piezoelectric section towards the load deviates from $Z_x$, one gets resonances when the sum of the roundtrip propagation phase ($2\,kL_x$) through the high impedance section and the phases of the reflection coefficients at the load and back interfaces of the high impedance section, is a whole number of $2\pi$. Here $k=\omega/c$ is the wave number at the angular frequency $\omega$ in the piezoelectric section with wave propagation velocity c.

With proper placement of electrodes as discussed under point 2 below, the resonance gives improved phase of the electric impedance of the electric port, hence giving improved sensitivity of the transducer in the resonant bands. According to the invention, thickness resonances in the high impedance section is used to boost the transduction efficiency at the lower and upper frequencies where the load matching section starts to become inefficient, hence increasing the active transduction band of the transducer. To achieve this effect, the thickness of the high impedance section is increased by added elastic layers, introducing resonances of this section on the low and high side of the efficient band of the load matching.

The added elastic layers in the high impedance section can be loaded or unloaded piezoelectric layers, which already have the same characteristic impedance as the other piezoelectric layers of this section. The characteristic impedance of composite piezoelectric materials can also be brought down in the 12–20 MRayl range, where one can find other materials with similar characteristic impedances, like aluminum (Al: $Z_0$~17.3MRayl) and magnesium (Mg: $Z_0$~10MRayl) materials, and the semiconductor silicon (Si: $Z_0$~19.5MRayl). Conducting metals and highly doped Si can also be used as electrodes in the structure, and transistor amplifiers and switches can also be integrated on Si-layers. Excitation of transversal modes and shear waves in the elastic layers can introduce problems, depending on the dimensions. In such cases, the invention devices a solution to attach layers of silver (Ag: $Z_0$~38MRayl), zirconium (Zr: $Z_0$~30.1MRayl), or zinc (Zn: $Z_0$~39.6 MRayl) directly to the undiced, whole ferrolectric ceramic material. Other actual materials are alloys like brass ($Z_0$~36MRayl) or cast iron ($Z_0$~33MRayl). These materials have characteristic impedances that are sufficiently close to the ceramic materials, and can be diced together with the ceramic layers to form a final metal/ceramic/polymer composite. The elastic layers of the metal/polymer composites can then be used as part of the electrodes as they provide metallic connection directly to the ferroelectric ceramic slabs, as discussed below. The invention also devices similar methods for manufacture of high impedance load matching layers with reduced lateral coupling. Mixtures of polymer with tungsten or other heavy powders can also be used for elastic layers in the high impedance section, albeit they have larger power absorption and hence reduces sensitivity compared to the other solutions.

2. Electrode placement. Conducting electrode layers are inserted at the surface of the piezoelectric layers in the high impedance section, to divide the high impedance section into elastic and piezoelectric layers separated by the electrodes. Two such electrode layers with an intermediate piezoelectric layer, constitute an electric layer port. The placement of the electrodes are selected so that for the active frequency bands of the port, a high thickness vibration amplitude of the piezoelectric layers between the electrodes is found.

For widest possible bandwidth, the back electrode is located at the interface between the backing mount and the high impedance section (no matching layers to the backing), as this location for all frequencies is either an antinode (for low impedance backing) or a node (for high impedance backing). The other electrode is then at the center of the actual frequency band selected at the antinode in front of the backing interface. This gives maximal thickness vibrations of the material between the electrodes at the center frequency, and as the back electrode is stationary relative to the standing wave pattern, we get a widest possible bandwidth of the electric pick-up.

Maximal electric pick-up is also obtained when there is an uneven number of half wave lengths between the electrodes when the back electrode is at an antinode (low backing impedance), or an uneven number of quarter wavelengths when the back electrode is at a node (high back impedance). In some situations one wants to use a limited transduction bandwidth of the transducer to filter the ultrasound pulse, for example to attenuate $2^{nd}$ and $3^{rd}$ harmonic components in the transmitted pulse with harmonic imaging. This can be furthered by positioning the back and front electrodes so in the standing wave pattern, that they vibrate with the same phase and amplitude at these frequencies.

3. Combining electric ports. The high impedance piezoelectric section can contain several piezoelectric layers covered with electrodes to form one electric port per layer. The signals for several electric layer ports are then favorably combined to influence the overall transfer function. The simplest examples are that the electrodes are galvanically connected to form a series or parallel coupling of two or more electric layer ports into a new electric resultant port. Coupling the electrodes of the layers together so that the voltages across the layers are the same (with voltage polarity defined relative to the polarization direction of the piezoelectric material), and the current into the resultant port is the sum of the currents in the layer ports, one obtains electrical parallel coupling of the layers. Coupling the electrodes of the layers together so that the voltage across the resultant electric port is the sum of the voltages across the layer ports, while the currents in the layer ports are the same as the current in the resultant port, gives an electric series coupling of the layers. In this galvanic coupling of the ports, it might be necessary to isolate electrodes between neighboring layers, or use opposite direction of the polarization of neighboring layers according to well known principles. One can also at transmit steer the voltages on individual electrodes so that one selectively obtain electrical parallel or series coupling of electric layer ports, as described in FIG. 12. Electrical anti-serial and anti-parallel coupling of the ports, where the currents or the voltages, respectively, of the ports have opposite polarity, are also actual to obtain specific transfer function as described in the specification below.

With galvanic coupling of the electrodes, the current in one set of layers influences the current in other layers so that one gets electrical coupling of the vibrations of all participating layers in the resultant port. Other types of combinations of the layer ports or resultant ports in receive mode, can be obtained by combining the signals after preamplifiers from the layer ports, possibly after filtering of the signals, into composite signal ports as described in FIG. 12. In this case the vibrations of the participating layers are unmodified by the combination.

One hence typically can have situations where layer ports are galvanically combined to produce resultant multi-layer ports, for example by parallel coupling of layer ports to obtain reduced electric impedance of the galvanic resultant ports. These galvanic resultant ports can again be combined electronically to form new composite ports that are electronically selectable.

The invention hence describes a general transducer concept that can be adapted for efficient operation of a single transducer in such a wide band of frequencies that multi frequency band operation can be achieved with the same transducer. The patent also applies to the design of individual elements of an ultrasonic transducer array. The description below shows specific designs based on the general principle introduced, that is particularly useful for sub, second, third, and fourth harmonic measurements and imaging, and combinations thereof.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference numerals denote similar elements throughout the various Figures:

FIG. 6*a* shows the amplitude for ideal matching between the load and the high impedance section, while

FIG. 7 shows the amplitude of the structure transfer and the electrode transfer functions, where

FIG. 8 shows example transducer according to the invention, where

FIG. 10 shows examples of practical transmit transfer functions for the electric ports of the example transducer in FIG. 8, where

FIG. 11 shows examples of receive transfer functions, where FIG. 11*a* shows the receive transfer functions of Port II and Port IV of FIG. 8, while

FIG. 12 shows an example transceiver structure according to the invention which allows electronic selection of electro-acoustic transfer functions, where

FIG. 13 shows an example transducer according to the invention, with a single piezoelectric layer, where

DETAILED DESCRIPTION OF THE PRESENTLY PREFERRED EMBODIMENTS

Background Theory

Figure 1:
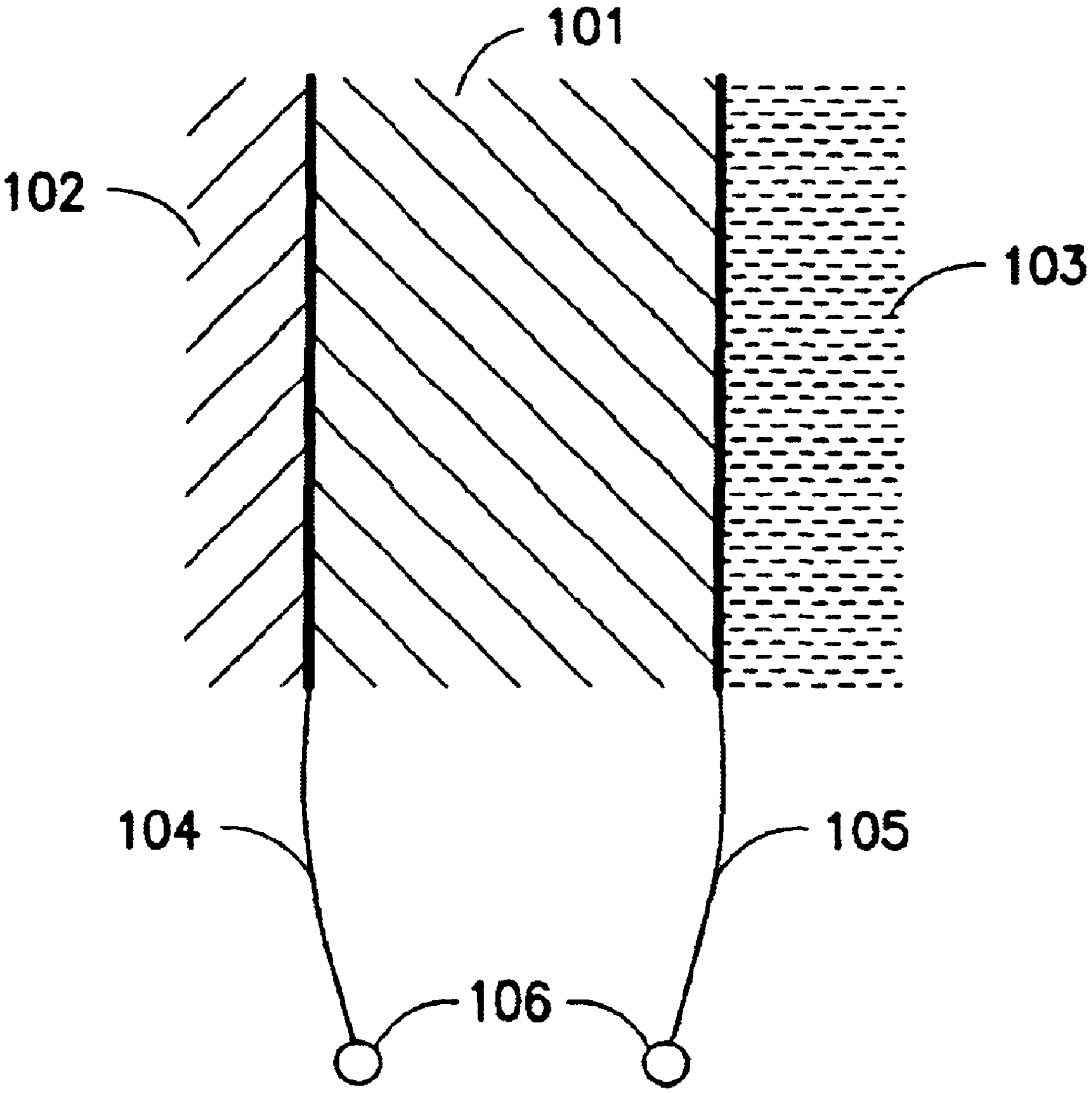
FIG. 1 shows an example of a piezoelectric plate covered with metal electrodes where the faces are in contact with a load and a backing material.

The simplest form of a piezoelectric ultrasound transducer is a piezoelectric plate, illustrated as 101 in FIG. 1, and connects directly to a tissue load material 102. For mechanical support, and also in some cases for acoustic purposes, the transducer is mounted on a backing material 103. For electromechanical coupling, both faces of the plate are coated with electrodes 104 and 105 that forms an electric port 106. The transducer is hence a two-port where the front face constitutes the first, acoustic port, and the electrodes forms the second, electric port.

Figure 2A:
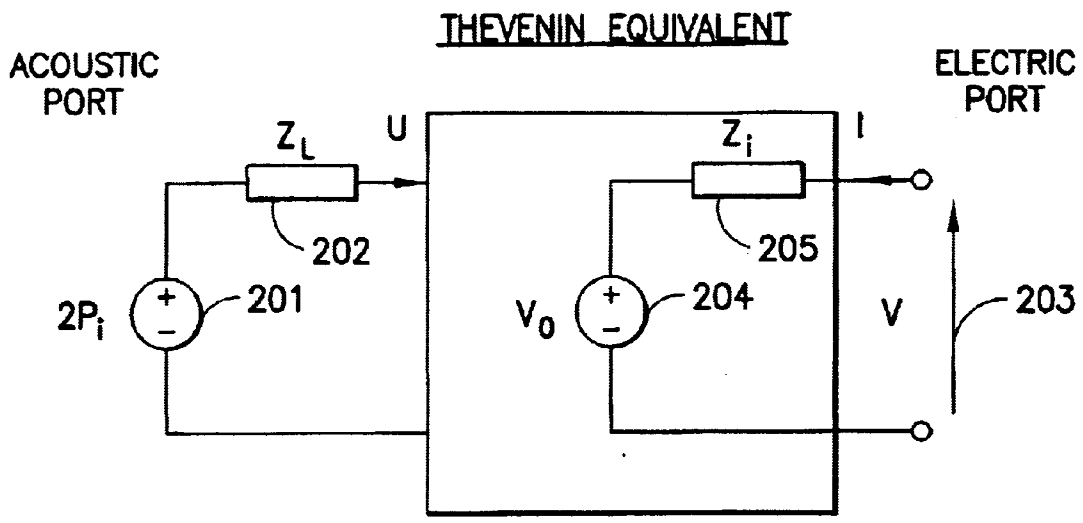
FIG. 2 shows representations of an ultrasound receiver transducer with an incident acoustic wave by two equivalent circuits, where a) shows a Thevenin equivalent while b) shows a Norton equivalent.

In the following we shall carry through the analysis with continuous, time harmonic signals with angular frequency ω. We calculate the values for a transducer with unit area, i.e. the currents, charges and admittances (i.e. the inverse of impedances) are given per unit area. An incident pressure wave in the tissue with amplitude $P_i$ and phase fronts co-planar with the transducer surface, can be represented as in FIG. 2*a* by a concentrated pressure source 201 with open terminal pressure $2P_i$ and source resistance 202, that is the characteristic impedance $Z_L$ of the source material. Such a wave excites vibrations in the transducer plate, with thickness vibration velocity $U_T$. For the actual pressure and currents, a linear representation of the piezoelectric material law is adequate, which gives $$U_T(\omega) = H_{Uo}(\omega)2P_i + H_Q(\omega)\frac{hI}{i\omega} \tag{1}$$

where I is the current at the electric port 203, h is the piezoelectric constant and i is the imaginary unit. $H_{Uo}$ is the transfer function from $2P_i$ to $U_T$ at zero current, and $H_Q$ is the transfer function from $hI/i\omega = hQ$ to $U_T$ with no incident wave $$H_{Uo}(\omega) = \frac{U_T(\omega)}{2P_i}\bigg|_{I=0} \tag{2}$$

$$H_Q(\omega) = \frac{U_T(\omega)}{hQ(\omega)}\bigg|_{P_1=0}$$

The thickness vibrations in the piezoelectric plate produces a receiver voltage, V, which is related to $U_T$ and I as $$V(\omega) = -\frac{h}{i\omega}U_T(\omega) + \frac{I(\omega)}{i\omega C_0} \tag{3}$$

where $C_0 = \in^S/L$, is the electric capacitance of the active piezoelectric layer with clamped (constant) thickness, $\in^S$ is the dielectric constant with clamped faces, and L is the thickness of the piezoelectric layer.

Inserting Eq.(1) into Eq.(3) we get $$V = V_o(\omega) + Z_i(\omega)I \tag{4}$$

$$V_o(\omega) = -\frac{h}{i\omega}U_{To}(\omega) = -\frac{h}{i\omega}H_{Uo}(\omega)2P_i$$

$$Z_i(\omega) = \frac{1}{i\omega C_0}\left(1 + i\frac{h^2 C_0}{\omega}H_Q(\omega)\right) = \frac{1}{i\omega C_0}\left(1 + i\frac{k_t^2 Z_x}{kL}H_Q(\omega)\right)$$

where $k_t^2 = h^2 \in^S/c^D$ is the electromechanical coupling coefficient, with $c^D$ as the elastic stiffness constant at constant charge, $Z_x = \{\rho c^D\}^{1/2}$ is the characteristic impedance of the piezoelectric material where ρ is the mass density of the piezoelectric material. $kL = \omega L/c$ where $c = \{c^D/\rho\}^{1/2}$ is the wave propagation velocity in the piezoelectric layer with constant charge on the electrodes. The electric port can hence be expressed as a Thevenin equivalent shown in FIG. 2*a* with unloaded voltage source $V_o$ at 204 and source impedance $Z_i$ at 205.

With shorted electrodes, we get a transducer output current as $$I_s(\omega) = hC_0U_{Ts}(\omega) = hC_0H_{Us}(\omega)2P_i$$

$$H_{Us}(\omega) = \frac{U_T(\omega)}{2P_i}\bigg|_{V=0} \tag{5}$$

Figure 2B:
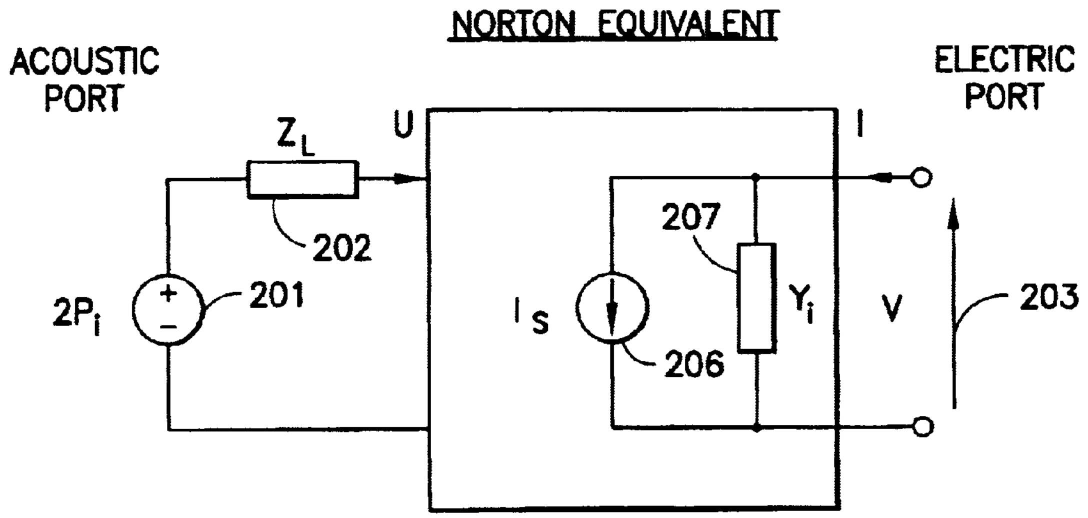
Figure 3A:
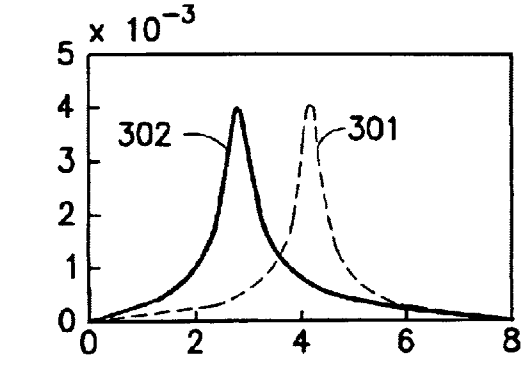
FIG. 3 shows relations between the thickness vibration velocity transfer functions of the piezoelectric layer and the electric source impedance for an acoustically unmatched and an acoustically matched transducer.
Figure 3B:
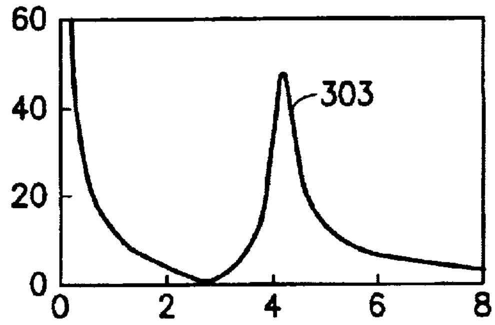
Figure 3C:
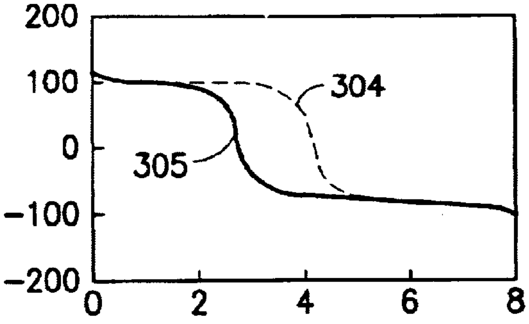
Figure 3D:
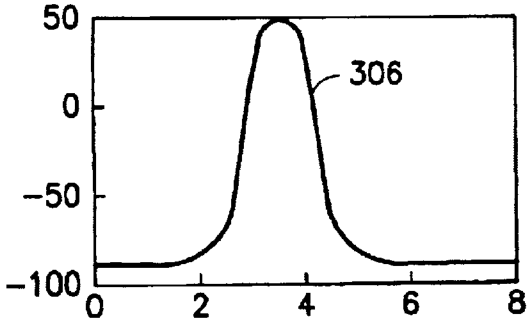
Figure 3E:
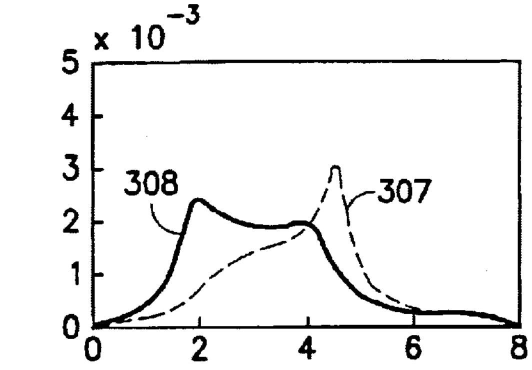
Figure 3F:
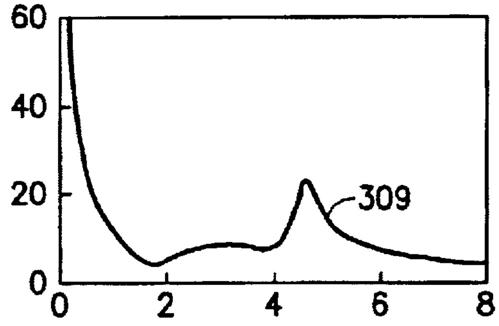
Figure 3G:
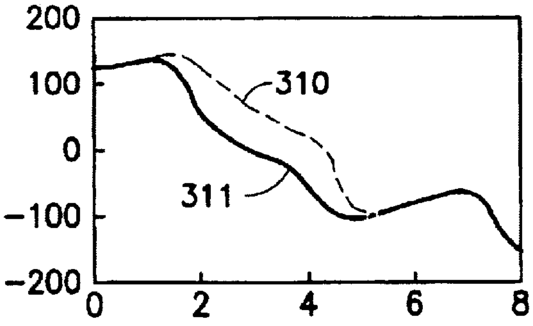
Figure 3H:
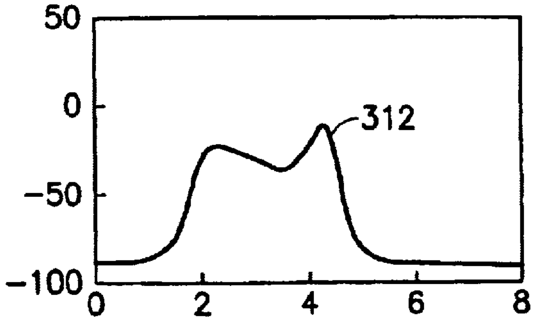

The electric port can hence be represented by the Norton equivalent circuit in FIG. 2*b* with shorted current source $I_s$ at 206 and source admittance $Y_i = 1/Z_i$ at 207. We note that the source impedance can be defined through $V_o(\omega) = -Z_i(\omega) I_s(\omega)$ as $$Z_i(\omega) = -\frac{V_o(\omega)}{I_s(\omega)} = \frac{1}{i\omega C_0}\frac{H_{Uo}(\omega)}{H_{Us}(\omega)} = \frac{1}{\omega C_0}\left|\frac{H_{Uo}(\omega)}{H_{Us}(\omega)}\right|e^{i(\phi_U(\omega)-\pi/2)} \tag{6}$$

where $\phi_U(\omega)$ is the phase lag between $H_{Uo}(\omega)$ and $H_{Us}(\omega)$ so that the phase of the source impedance is $\theta_i(\omega) = \phi_U(\omega) - \pi/2$. As the source impedance phase angle $\theta_i(\omega) > -\pi/2$ we must have $\phi_U(\omega) > 0$. We also note that at short circuit thickness resonance of the piezoelectric plate we get $|H_{Us}|$ large, which implies that $|Z_i|$ is small, while with open circuit thickness resonance of the plate we get $|H_{Uo}|$ large, which implies that $|Z_i|$ is large.

We define the transducer short circuit and open circuit receive transfer function as $$H_{tt}(\omega) = \frac{I_s(\omega)}{2P_i} = hC_0 H_{Us}(\omega) \tag{7}$$

$$H_{ot}(\omega) = \frac{V_o(\omega)}{2P_i} = -\frac{h}{i\omega} H_{Uo}(\omega)$$

When the transducer electrodes are driven with a voltage $V_{tt}$ in transmit mode, one will due to reciprocity get the following transmit transfer function between $V_{tt}$ and the vibration velocity U of the front surface of the whole transducer structure $$U(\omega)=H_{tt}(\omega)V_{tt} \tag{8}$$

The pressure to open circuit voltage (I=0) transfer function is defined as $$H_{ot}(\omega) = \frac{V_o(\omega)}{2P_i} = -\frac{Z_i(\omega)I_s(\omega)}{2P_i} = -Z_i(\omega)H_{tt}(\omega) \tag{9}$$

where the relation to $H_{tt}$ is obtained from the Norton equivalent in FIG. 2*b*. Terminating the electric port with a receiver impedance $Z_r(\omega)$, the incident pressure to receiver voltage transfer function becomes $$H_{rt}(\omega) = \frac{V(\omega)}{2P_i} = -\frac{H_{ri}(\omega)I_s(\omega)}{2P_i} = -H_{ri}(\omega)H_{tt}(\omega) \tag{10}$$

$$H_{ri}(\omega) = \frac{Z_r(\omega)Z_i(\omega)}{Z_r(\omega)+Z_i(\omega)}$$

where $H_{ri}$ is the parallel coupling of $Z_r$ and $Z_i$. We also note that $H_{rt}$ is related to $H_{ot}$ as $$H_{rt}(\omega) = \frac{Z_r(\omega)}{Z_r(\omega)+Z_i(\omega)} H_{ot}(\omega) \tag{11}$$

The available power from the electric port is $$P_{el,av} = \frac{|V_o|^2}{8\mathrm{Re}\{Z_i\}} = \frac{h^2 C_0 |H_{Uo}|^2}{2\omega\mathrm{Im}\{H_{Uo}/H_{Us}\}} P_i^2 = \frac{h^2 C_0 |H_{Uo}||H_{Us}|}{2\omega\sin\phi_U} P_i^2 = \frac{k_t^2 Z_x |H_{Uo}||H_{Us}|}{2kL\sin\phi_U} P_i^2 \tag{12}$$

We note that $\sin\phi_U=\cos\theta_i$, where $\theta_i$ is the phase of $Z_i$. The available acoustic power in the incident wave is $$P_{ac} = \frac{P_i^2}{2Z_L} = \frac{Y_L P_i^2}{2} \tag{13}$$

where $P_i$ is the pressure amplitude of the incident acoustic wave in the tissue, and $Z_L=1/Y_L$ is the acoustic impedance of the tissue material. The maximal acoustic to electric power conversion efficiency of the transducer is hence $$\eta_{ae}(\omega) = \frac{P_{el,av}(\omega)}{P_{ac}} = h^2 C_0 Z_L |H_{Uo}(\omega)| \frac{|H_{Us}(\omega)|}{\omega\sin\phi_U(\omega)} = k_t^2 Z_x Z_L |H_{Uo}(\omega)| \frac{|H_{Us}(\omega)|}{kL\sin\phi_U(\omega)} \tag{14}$$

where due to reciprocity, the efficiency on transmit is equal to the efficiency on receive.

To make $\eta_{ae}$ close to unity, we hence must make $|H_{Uo}||H_{Us}|$ large and it appears at first sight that $\phi_U$ close to zero would also help. This is equivalent to the phase angle of the input impedance, $\theta_i$, being close to $-\pi/2$. However, $\phi_U$, $|H_{Uo}|$ and $|H_{Us}|$ are dependent as seen from FIG. 3, which in practice implies that the ratio is high when the phase angle $\theta_i$ of $Z_i$ is close to zero. Also, when $\theta_i$ is close to $-\pi/2$, i.e. close to capacitive source impedance, the matching network for complex conjugate matching will introduce non-negligible losses so that the theoretical value of efficiency in Eq.(14) will not be reached. When $\theta_i$ approaches $-\pi/2$, it is also difficult to implement a complex conjugate matching impedance over a larger band of frequencies. This complicates pulse transmission through the transducer, making it difficult to avoid ringing of the transmitted pulses.

For efficient acousto-electric coupling it is therefore desirable to have $\theta_i$ substantial larger than $-\pi/2$, preferably $>-\pi/4$ and approaching zero, in the actual frequency band. This requires that $\phi_U>\pi/4$, approaching $\pi/2$.

The physical background for $\phi_U$ is that the temporal variation of the thickness vibration velocity lags a phase angle $\phi_U$ when the termination of the electrodes is changed from open to shorted. This phenomenon is explained in more detail in relation to FIG. 3, where 301 shows typical variations of $|H_{Uo}|$ around the resonance frequency and 302 shows $|H_{Us}|$ as a function of frequency. We note that shorting the electrodes moves the peak of the resonance around 0.7 downwards in frequency. The amplitude $|Z_i|$ of the electrical input impedance is obtained from Eq.(5) as the curve 303 in the Figure. We note that the peak of $|Z_i|$ is given by the resonance in $|H_{Uo}|$ while the bottom of $|Z_i|$ is given close to the resonance in $|H_{Us}|$. In 304 is shown the phase of $H_{Uo}$, which varies from ~+90 deg ($+\pi/2$) below the resonance to ~−90 deg ($-\pi/2$) above the resonance. Shorting the electrodes, the phase variation of $H_U$ is changed to that of $H_{Us}$ shown as 305 of the Figure. 306 in the Figure shows the phase of the electrical input impedance as $\angle Z_i=\angle H_{Uo}-\angle H_{Us}-\pi/2$, where $\angle$ indicates the phase of the complex function. We hence see that the frequency range where $\angle Z_i$ is substantially higher than $-\pi/2$, is determined by the distance between the open circuit and short circuit resonance of the plate. This frequency range is essentially the effective bandwidth of the transducer, and is determined by the electromechanical coupling efficiency of the piezoelectric material.

Figure 4:
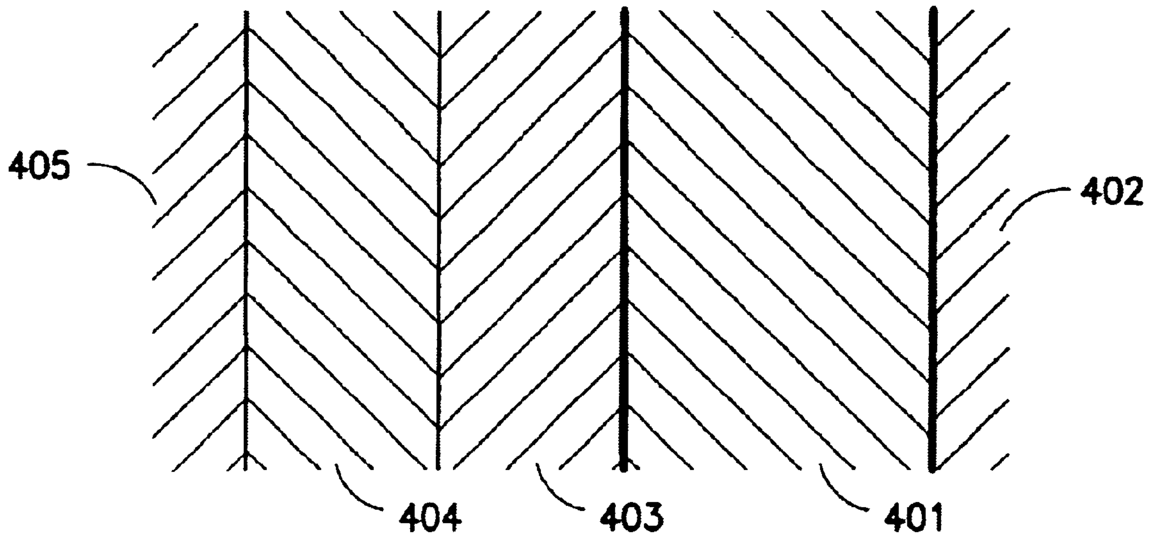
FIG. 4 shows a cross section of a typical, acoustically matched transducer.

As described above, the effective bandwidth of the transducer can be increased by more efficient coupling of energy out of the vibrating plate through impedance matching layers between the plate and the acoustic load material as shown in FIG. 4. This Figure shows a piezoelectric plate 401 mounted on a backing material 402 with two elastic impedance matching layers 403 and 404 between the piezoelectric plate and the acoustic load material 405.

Figure 12A:
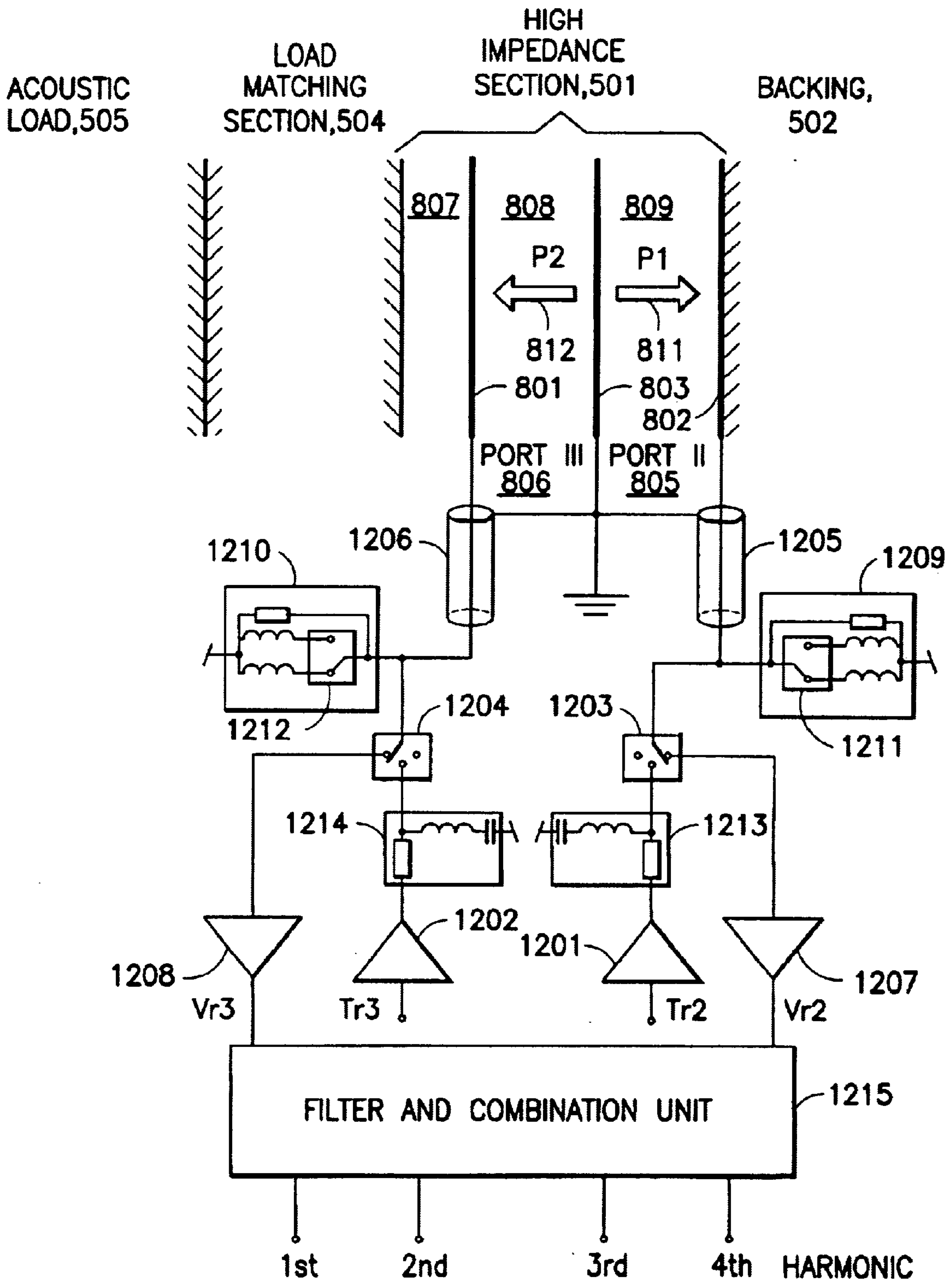
FIG. 12*a* shows a block diagram of the transceiver structure.
Figures 1, 12B:
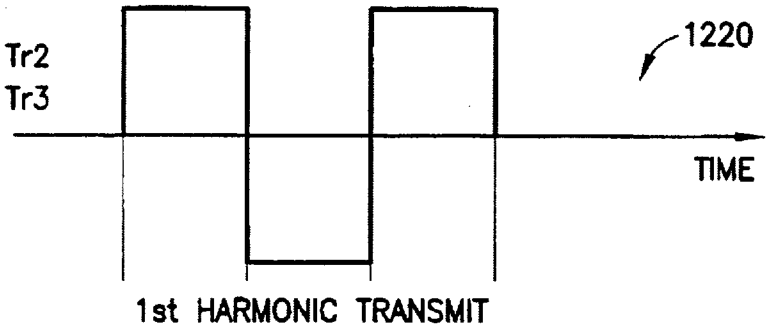
FIGS. 12*b* and 12*c* show example drive signals for the transmit amplifiers to select interesting transfer functions.
Figures 2, 12B:
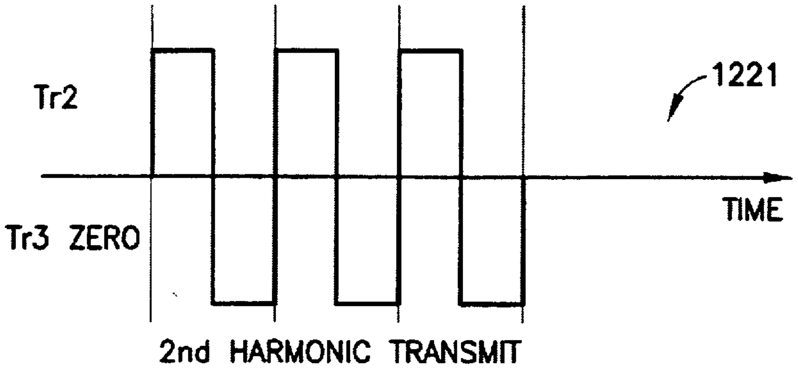
Figures 3, 12B:
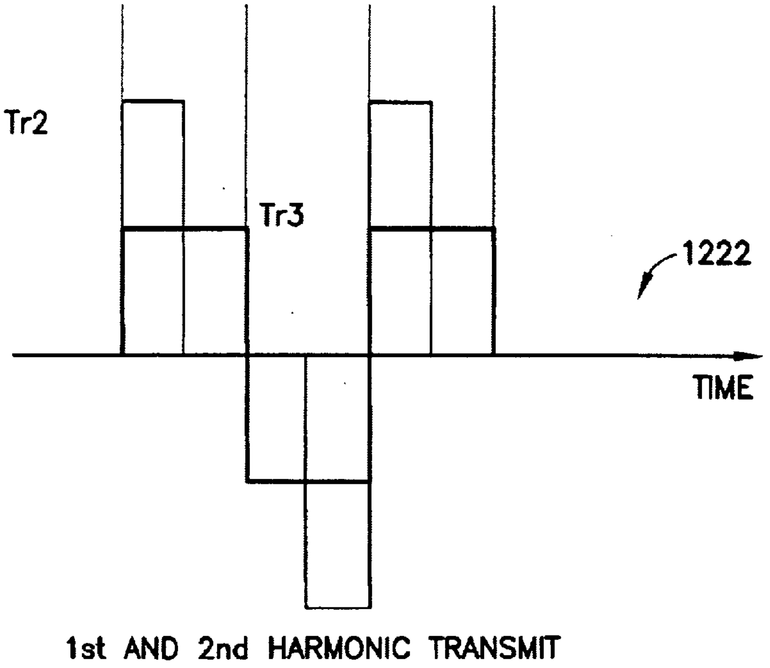

The matching layers make the coupling of vibration energy from the piezoelectric plate to the load more efficient, hence widening the resonance peaks of the thickness vibration velocities at open, $H_{Uo}$, and shorted, $H_{Us}$, electric port, shown as 307 and 308 in FIG. 3. The increased losses of plate vibration energy, also makes the phase variation $\angle H_{Uo}$, shown as 310, and $\angle H_{Us}$, shown as 311, less steep than for the lower loss situation in 304 and 305, respectively. The resulting module $|Z_i|$ and phase $\angle Z_i$ of the electric input impedance is given according to Eq.(6) as 309 and 312 in the Figure.

We note that due to increased power losses to the load material one gets a less sharp resonance with lower peak amplitudes of $|H_{Uo}|$ and $|H_{Us}|$ than for the plate without matching in 301 and 302. We also note that the less steep variation of $\angle H_{Uo}$ and $\angle H_{Us}$ makes $\angle Z_i$ high for a wider frequency band, with less peak value compared to the lower loss situation in 306. Increasing the characteristic impedance of the backing layer 402 will provide a similar increase in the widths of resonance peaks with reduced vibration amplitudes.

We hence see that impedance matching to the load, gives some, but limited increase in the efficient bandwidth of the transducer, at the cost of reducing the peak value of $\angle Z_i$. This is due to a slower variation of $\angle H_{Uo}$ and $\angle H_{Us}$ with frequency, which keeps the area between the $\angle Z_i$ and $-\pi/2$ close to constant during this increase in the bandwidth. The difference between the open circuit and short circuit resonance frequencies, $\omega_o$ and $\omega_s$, determined by $k_t$, hence plays a dominant role in defining the area between the $\angle Z_i$ and $-\pi/2$, and hence also maximal efficient bandwidths that can be obtained with such transducers.

The Present Invention

The invention provides a new design of ultrasound transducers and transducer arrays with available ferro-/piezoelectric materials that provides an increased efficient bandwidth of operation. The principle of the invention is described with reference to FIG. 5, where section 501 includes one or more piezoelectric layers to be used for acousto-electric energy coupling, and possibly also purely elastic layers with close to the same characteristic impedance. As the characteristic impedance of the piezoelectric layers, $Z_x$, is higher than that for the load material, this section has the highest characteristic impedance in the structure and is referred to as the high impedance section.

Characteristic for the high impedance section is that it behaves as a unity for thickness resonances with unloaded electric ports, so that resonances are determined by its total thickness $L_x$. To obtain such a unity, the layers in the high impedance section must have close to the same characteristic impedance, so that one can neglect internal reflections within the section. In this respect, one should note that a reflection coefficient less than 10% at an interface, requires that the deviation in the characteristic impedance of the interfacing materials must be less than 20%. One hence can use this limit as a "fuzzy" guide to define "close to the same characteristic impedance".

With composite ceramic/polymer piezoelectric materials, the characteristic impedance can be brought down to ~12–20 MRayl. There are several alloys or pure forms of aluminum (Al) and magnesium (Mg) that produce characteristic impedances that are within 20% of this range (Al: $Z_0$~17.3MRayl, MG: $Z_0$~10MRayl), and hence can be used as elastic layers within the high impedance section of such transducers. These materials can also be used for electrodes in a combined electrode and elastic layer. Al can then be grown to adequate thickness by electroplating directly on for example a sputtered Al layer on the composite ceramic/polymer layer. Adequate thickness Mg layers can be grown by electroplating in a high temperature (~450° C.) electrolytic bath, and added to the structure in its final thickness. Thin Al and Mg layers can also be obtained by milling down plates to the actual thickness, and added to the structure with its final thickness. The layer thickness can also be modified through lapping of the layers after they are added to the structure.

The semiconductor silicon (Si) has a characteristic impedance ~19.5 MRayl, and is hence a candidate to participate in the high impedance section, where controlled layer thicknesses can be obtained through etching. Integration of amplifiers and switches are then conveniently done on such a Si layer. Heavy doping of Si also makes it useful for electrodes.

The metal layers can be deposited to the right thickness through electroplating onto a sputtered metal layer, or adhered to a sputtered metal layer in its final thickness, or also with over thickness with reductions in thickness through etching or grinding. One can also engineer conducting thick film printing paste, for example as mixture of metal and glass powder, so that adequate characteristic impedance of the final, sintered film is obtained. This allows for thick film printing of elastic, conducting layers.

Other candidates of elastic materials to be used in the high impedance section are glasses and mixtures of polymer and metal powder, like tungsten, although mixed materials have higher absorption and reduces sensitivity of the transducer compared to the homogeneous materials of for example Al, Mg, and Si.

The high impedance layers are connected to a backing material 502, possibly through a back impedance matching section 503 composed of one or more elastic layers. Such matching to the backing can be used to increase the transducer sensitivity in selected frequency ranges, for example in the high frequency range, by reducing power transmitted into the backing in this range. The impedance transformation properties is defined by the layer thickness and characteristic impedance, which is selected according to known methods as described for the load matching below. The invention, however, devices new methods of manufacturing such elastic layers, as also described for the load matching below.

A problem with such back matching is that it reduces the overall bandwidth of the transducer. The back matching section 503 may therefore be missing for wide band operation, where the power transmitted into the backing is minimized by using a backing material with low characteristic impedance (~1 MRayl). This gives a vibration antinode at the back interface, or a high characteristic impedance (~30 MRayl) which gives a vibration node at the back interface.

The high impedance section 501 is connected on the front side to the acoustic load material 505 through a load impedance matching section 504, that raises the impedance $Z_{xm}$ seen on the front face of section 501 to adequate level, according to known methods. The load matching section is usually composed of several elastic layers with different characteristic impedances between that of the load material, $Z_L$, and the high impedance section 501, $Z_x$, as discussed below. Selection of thicknesses and characteristic impedances of the load matching can be done according to known methods, for example as described in relation to Eq.(24) below. The invention, however, devices a new method of manufacturing such layers, as described in more detail below.

Figure 5:
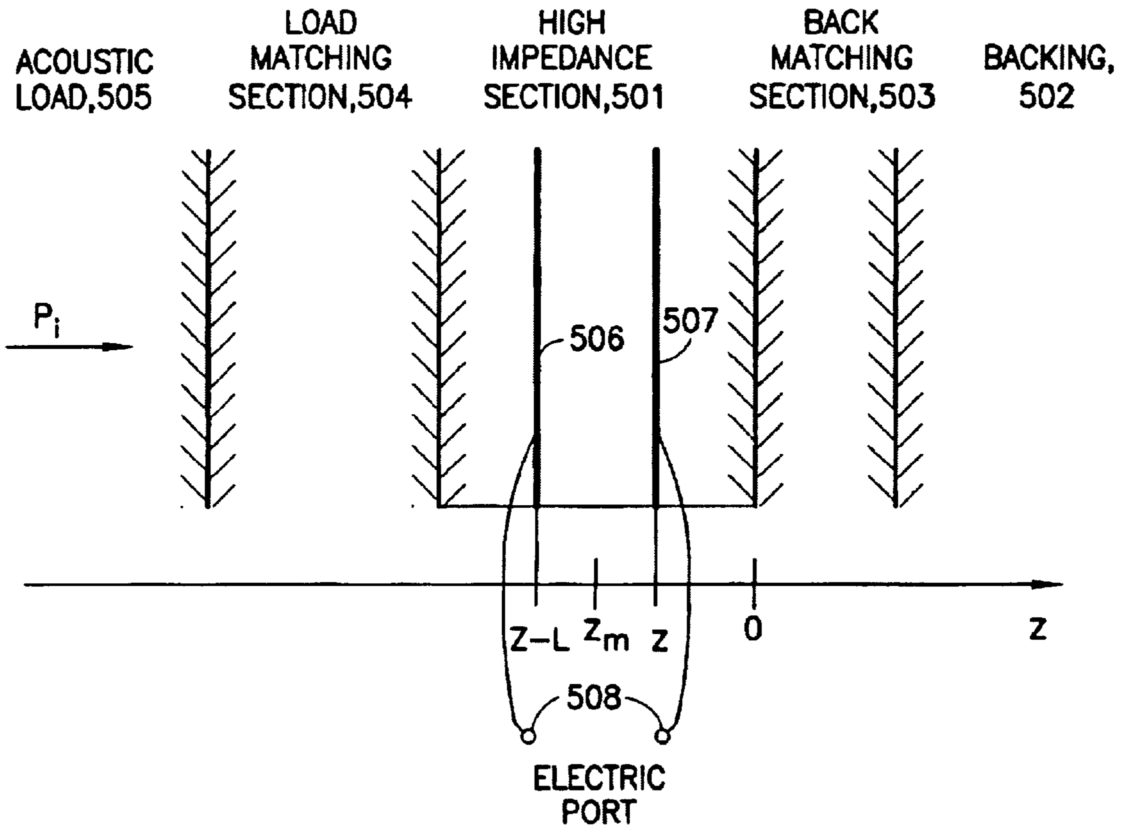
FIG. 5 shows a cross section of a transducer structure according to the invention.

To further describe the principles of the design, we express the vibration velocity waves in layer number n by the complex envelope $$U_n(z,\omega)=U_{n+}e^{-ik_nz}+U_{n-}e^{ik_nz}=(1+R_ne^{i2k_nz})U_{n+}e^{-ik_nz} \tag{15}$$

$$R_a=\frac{U_{n-}}{U_{n+}} \qquad k_n=\frac{\omega}{c_n}$$

where $c_n$ is the wave propagation velocity in the layer and $k_n$ is the wave number in the layer. z is the coordinate normal to the layers as defined in FIG. 5, and the real time vibration velocity is $u_n(z,t)=\mathrm{Re}\{e^{i\omega t}U_n(z)\}$. $R_n$ is the vibration velocity reflection coefficient at z=0. The absolute amplitude of the vibration velocity as a function of z hence becomes $$|U_n(z,\omega)|=\sqrt{U_{n(z,\omega)}U^*_{n(z,\omega)}}=|U_{n+}|\sqrt{+}e,rad\ 1+|R_n|^2+2|R_n|\cos(2k_nz+\phi_{Rn})+ee \tag{16}$$

where $\phi_{Rn}$ is the phase of $R_n$. We note that for $R_n$ 0 we get a standing wave component with antinodes (maxima) and nodes (minima) of $|U_n(z)|$ for $2k_nz+\phi_{Rn}=-2p\pi$ and $-(2p+1)\pi$ respectively, p=0, 1, 2, . . . . The distance between neighboring antinodes and nodes is hence $\lambda/4$. With negligible absorption in the material, $k_n$ is real, and the maximal and minimal amplitudes and the standing wave ratio $S_n$ are then $$|U_n|_{max}=|U_{n+}|(1+|R_n|)\ |U_n|_{min}=|U_{n+}|(1-|R_n|) \quad (17)$$

$$S_n=\frac{|U_n|_{\max}}{|U_n|_{\min}}=\frac{1+|R_n|}{1-|R_n|}$$

The complex reflection coefficient is defined as $$R_{cn}=\frac{U_{n-}e^{ik_nz}}{U_{n+}e^{-ik_nz}}=R_ne^{i2k_nz} \quad (18)$$

We then note that the antinodes and nodes of $|U_n(z)|$ are found at the locations z where $R_{cn}$ is real and positive or negative, respectively. Absorption makes $k_n$ complex, with an imaginary component that increases with ω. The amplitude of both the forward and the backward waves then reduces in their propagation direction, and $R_{cn}$ hence reduces in amplitude with diminishing z.

We now introduce an electrode layer 506 at location z−L and another electrode layer 507 at z inside the high impedance piezoelectric section. These electrodes define a piezoelectric layer with midpoint at $z_m=z-L/2$, front face electrode at $z-L=z_m-L/2$, and back face electrode at $z=z_m+L/2$, giving an electric port 508. The thickness vibration velocity for this layer is $$U_T(z_m,\omega)=U_n(z_m+L/2,\omega)-U_n(z_m-L/2,\omega) \quad (19)$$

Inserting Eq.(15) and further evaluation of this expression gives $$U_T(z_m,\omega)=-i2(1-R_ne^{i2k_nz_m})\sin(k_nL/2)\ e^{-ik_nz_m}U_{n+} \quad (20)$$

The transfer function from the incident pressure to the thickness vibration velocity can hence be written as (21)

$$|H_U(z_m,\omega)|=\frac{|U_T(z_m,\omega)|}{2P_i}=|H_{ele}(z_m,\omega)||H_{stru}(\omega)| \quad a)$$

$$|H_{ele}(z_m,\omega)|=2|\sin(k_nL/2)|\sqrt{\frac{1+|R_n|^2-2|R_n|\cos(2k_nz_m+\phi_{Rn})}{(1+|R_n|)^2}} \quad b)$$

$$|H_{stru}(\omega)|=\frac{|U_n|_{\max}(\omega)}{2P_i} \quad c)$$

where $H_{ele}$ is the electrode transfer function determined by the placement of the electrodes within the high impedance section, defined by the layer center $z_m$ and thickness L. $P_i$ is the amplitude of the incident wave in the load material, and in the definition of $|U_n|_{max}$ we have neglected the variation of $|U_n|_{max}$ with z due to absorption. $H_{stru}$ is called the structure transfer function, and is determined by the characteristic impedances and thicknesses of the matching layers, the characteristic impedance and thickness of the high impedance section, the impedance of the backing material, also possibly the characteristic impedances and thicknesses of layers in the back matching section, and the electric loading impedance of the active ports. With electric loading of the ports $H_{stru}$ will also depend on the placement of the electrodes, while with no electric loading (open ports) it is independent of electrode position.

The challenge is now to design the characteristic impedances and thicknesses of the matching layers, the thickness of the high impedance section, and the placement of electrodes in the high impedance section so that adequate acousto-electric transfer functions in defined frequency bands are obtained. With reference to Eq. (21) we see that this design challenge can be broken into three levels:

1. Design load and back matching sections and a high impedance section so that $|H_{stru}(\omega)|$ takes values in the defined frequency bands.
2. Place pairs of electrodes within the high impedance region so that $|H_{ele}(\omega)|$ takes values in the defined frequency bands. For wide band and multi-band operation it is then convenient to use several electrode pairs giving multiple electric ports, as follows from the description of the particular embodiments of the invention below.
3. Combine the signal from several electric ports either through galvanic contacting of the electrodes in series or parallel, or electronic summing of the signals from the electric ports after isolation amplifiers and proper filtering for each electric port, or a combination of both. The receive transfer functions can then be affected by electric impedance matching networks between the transducer and the receiver amplifiers. It is in many situations desirable, especially with small elements of a transducer array, to galvanically parallel couple neighboring layer ports to form an electric resultant port with lower electric impedance. The outputs of the resultant ports can then be combined after the receiver preamplifier, possibly after filtering, to form composite electric ports.

We shall now describe a particular embodiment according to the invention that provides four selectable frequency ranges for active electromechanical coupling. We first describe how to establish a $|H_{stru}(\omega)|$ so that the wide frequency range is covered, and then continue to select placement of the electrodes so that the desired frequency bands are obtained.

We start with defining the high impedance section with characteristic impedance $Z_x$, which is typically ~15 MRayl for ceramic/polymer composites. Then assume that we have an ideal impedance matching section that raises the impedance seen from the surface of the high impedance section towards the load to $Z_{xm}=Z_x$ in the actual frequency band. With no power losses in the load matching section, the matching raises the incident pressure at the interface to $$P_{xm}=P_i\sqrt{\frac{Z_{xm}}{Z_L}} \quad (22)$$

The incident wave is then reflected at the backing with a vibration velocity reflection coefficient $$R_B=\frac{Z_x-Z_B}{Z_x+Z_B} \quad (23)$$

For maximal sensitivity of the transducer, we want a minimal transmission of acoustic power into the backing. This requires either a backing impedance that is much lower or much higher than $Z_x$. When $Z_B<Z_x$, $R_B>0$ and the back interface becomes an antinode in the vibration pattern. When $Z_B>Z_x$, $R_B<0$ and the back interface becomes a node in the vibration pattern.

Arrays that are covered in a dome and hence are not pushed against a skin or other load materials, can be mounted on a feather light backing material, like a synthetic foam material, where $Z_B<<Z_x$. This will give $R_B>0$ and close to 1. A backing material with high characteristic impedance gives best mechanical support, and is desirable with transducer arrays that are in direct contact with the body. However, it is difficult to find absorbing backing materials with $Z_B>>Z_x$ so that the power transmission into the backing can be kept low, which implies that this type of backing gives power losses. A back impedance matching section can be used to further reduce transmission of power into the backing in selected frequency bands as discussed above, for example with a λ/4 layer of a high characteristic impedance metal that also can be used as an electrode. It would then be advantageous to use a metal that can be electroplated to the right thickness under controlled conditions. However, back impedance matching reduces the bandwidth of both the $H_{stru}$ and the $H_{ele}$ function due to the resonant nature of such a matching.

Figure 6A:
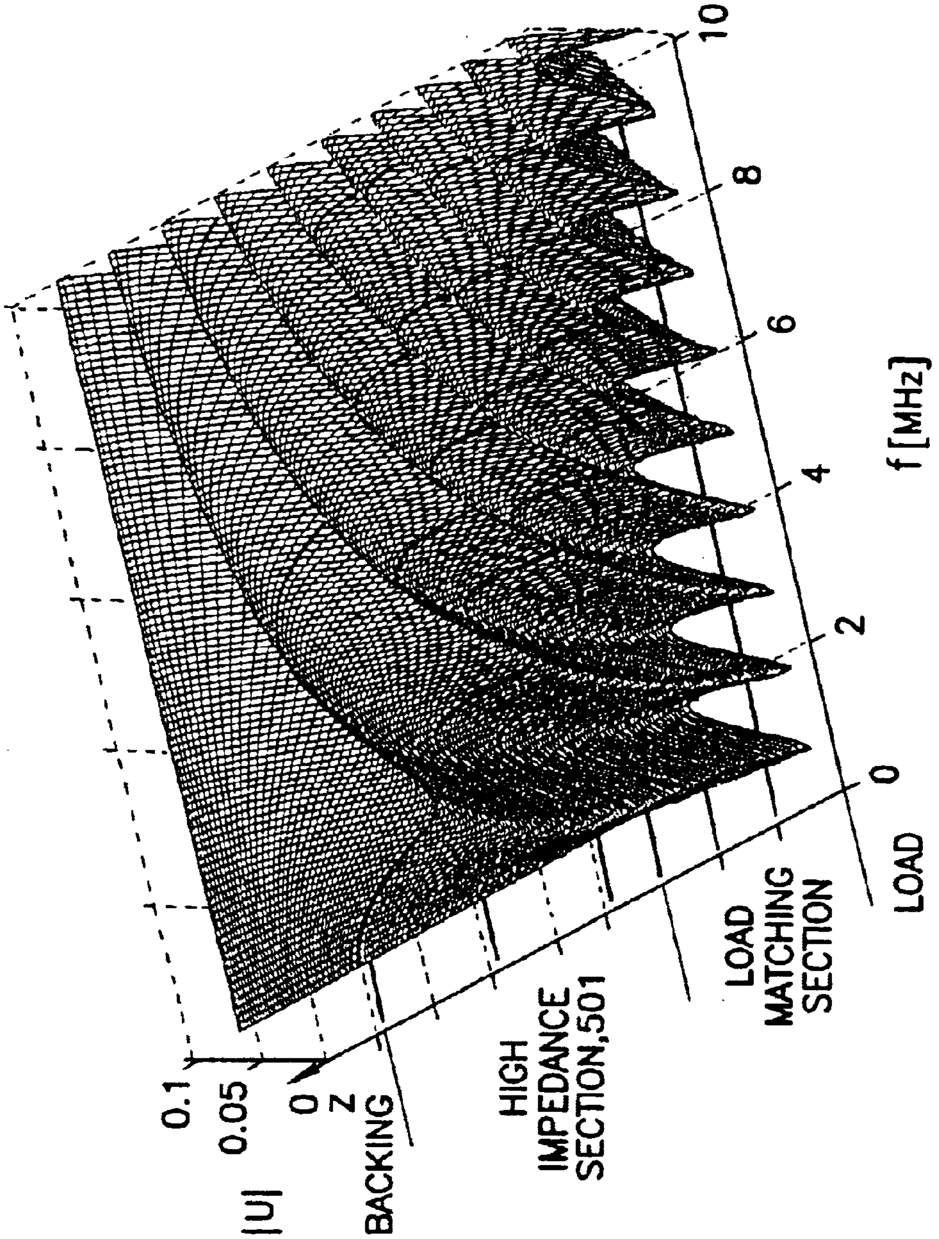

We hence start by assuming a real and low backing impedance $Z_B<<Z_x$ with no back matching section, so that $R_B$ is real and positive close to 1, independent of frequency as both $Z_x$ and $Z_B$ are frequency independent. The amplitude of the vibration velocity $|U_n(z,\omega)|$, as given in Eq.(16), is shown as the surface in FIG. 6*a* as a function of depth z in the structure and frequency $f=\omega/2\pi$. As $R_B$ is close to 1 we get a large standing wave ratio with a high $|U_n|_{max}$ and low $|U_n|_{min}$. We note that the interface to the backing is an antinode in the vibration pattern for all frequencies, because $Z_B$ and hence also $R_B$ is frequency independent. At $-\lambda/4$ distance from the backing towards the load we get a node with repetitive nodes at distance $z=-(2p+1)\lambda/4$ from the backing, p=1, 2, . . . . Similarly we get a second antinode at $-\lambda/2$ distance form the backing, with repetitive antinodes at distance $z=-p\lambda/2$ from the backing, p=2, 3, . . . . We note that as the frequency increases, the nodes and antinodes approach the backing on hyperbolas with distance to the backing of (2p+1)c/4f for the nodes and pc/2f for the antinodes, p=0, 1, 2, . . . .

Figure 7A:
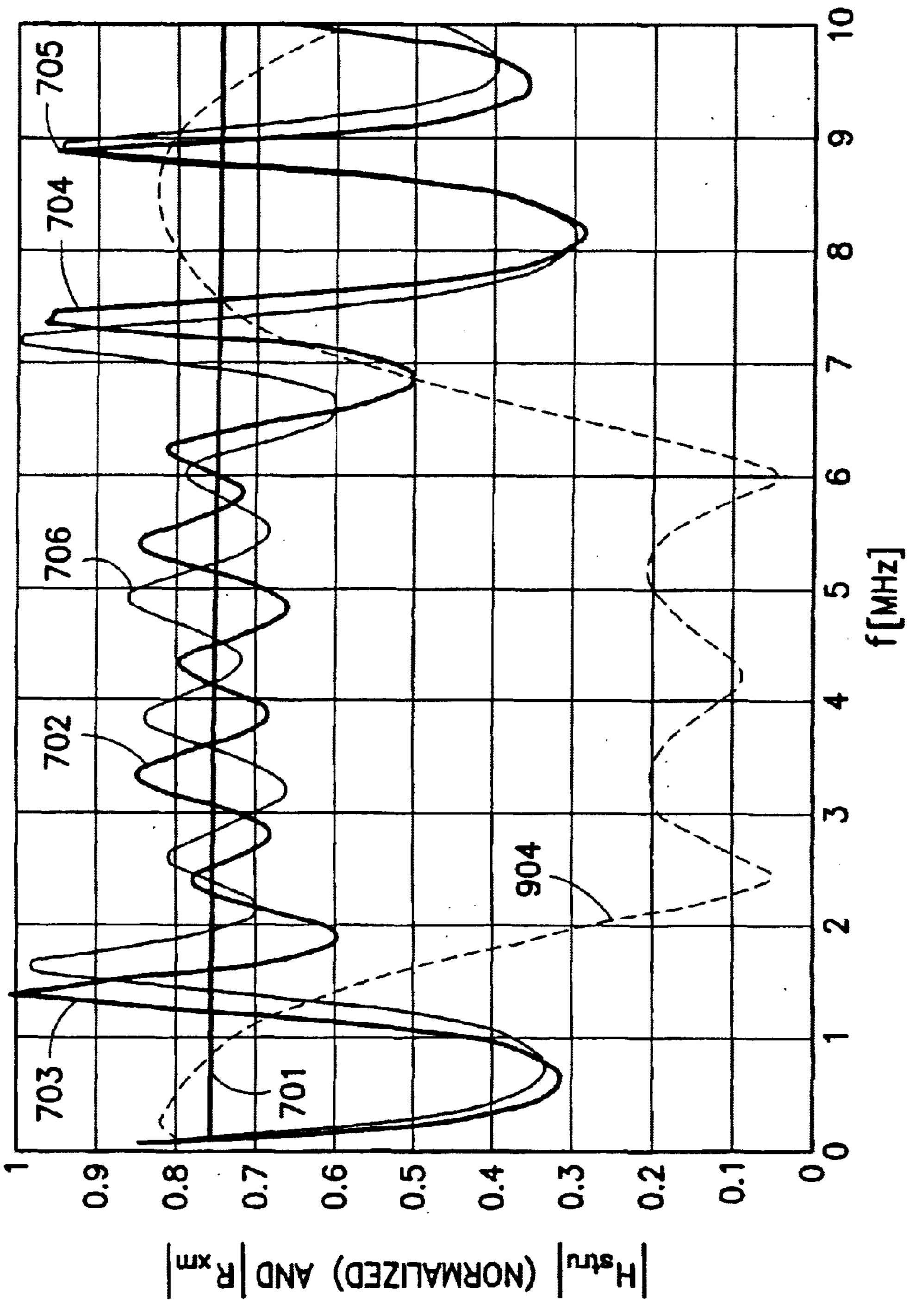
FIG. 7*a* shows the amplitude of the structure transfer function for ideal matching and practical matching between the load and the high impedance section.

Comparing with Eq.(21c) we see that $|H_{stru}|$ is given by the amplitude of the vibration velocity at the backing interface. As $Z_{xm}=Z_x$ within the actual frequency band, the reflection coefficient at the load face of the high impedance section is zero, and the structure has no resonance. With negligible power absorption in the layers, $|H_{stru}|$ becomes close to constant with frequency in this situation of ideal matching, shown as 701 in FIG. 7*a*. Power absorption in the structure, adds a steady fall of $|H_{stru}|$ with increasing frequency.

Figure 8A:
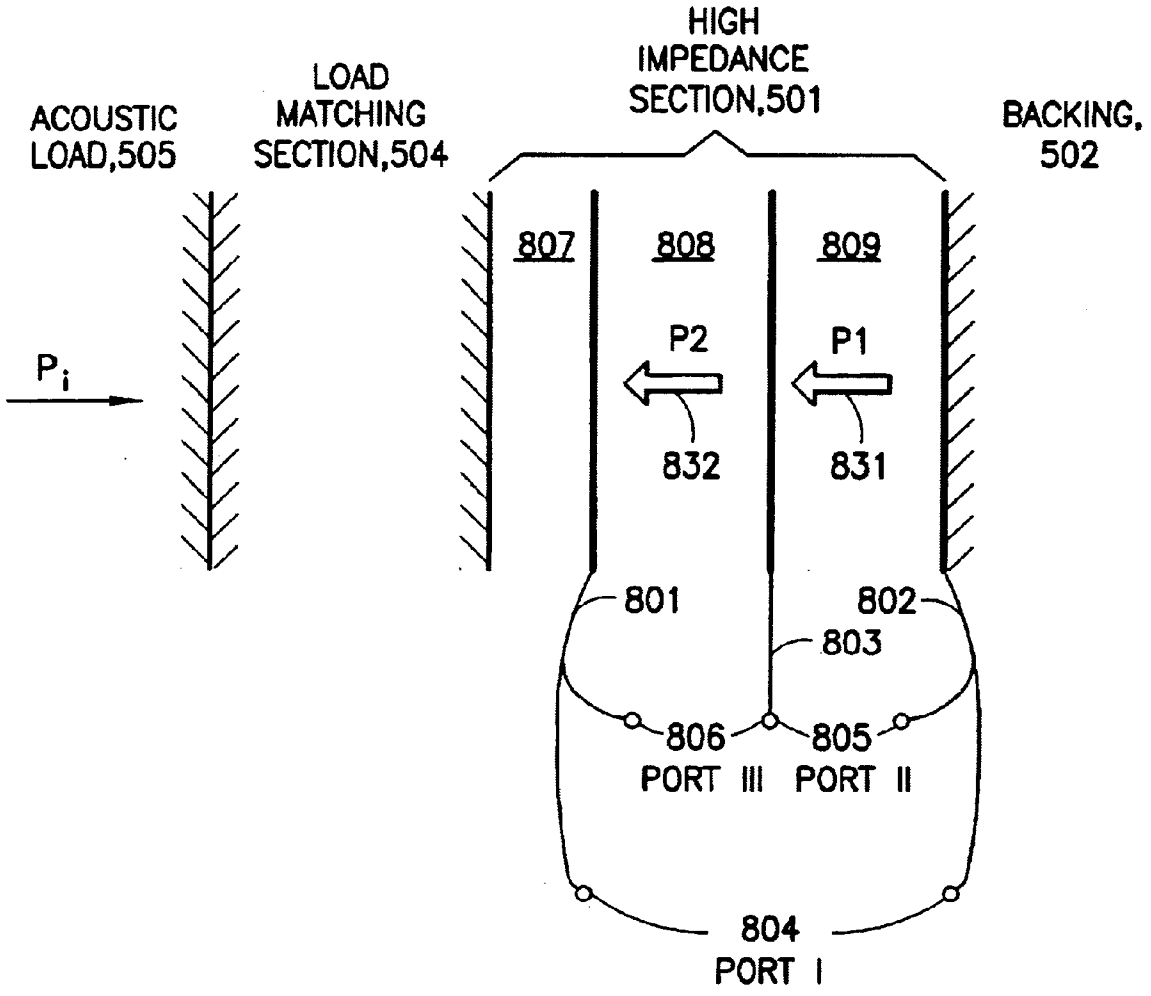
FIG. 8*a* shows a schematic cross section of an example transducer according to the invention, where the high impedance piezoelectric section is specified as two piezoelectric layers, and an added elastic layer, the faces of the piezoelectric layers are covered with three electrodes that constitutes three electric ports.
Figure 8B:
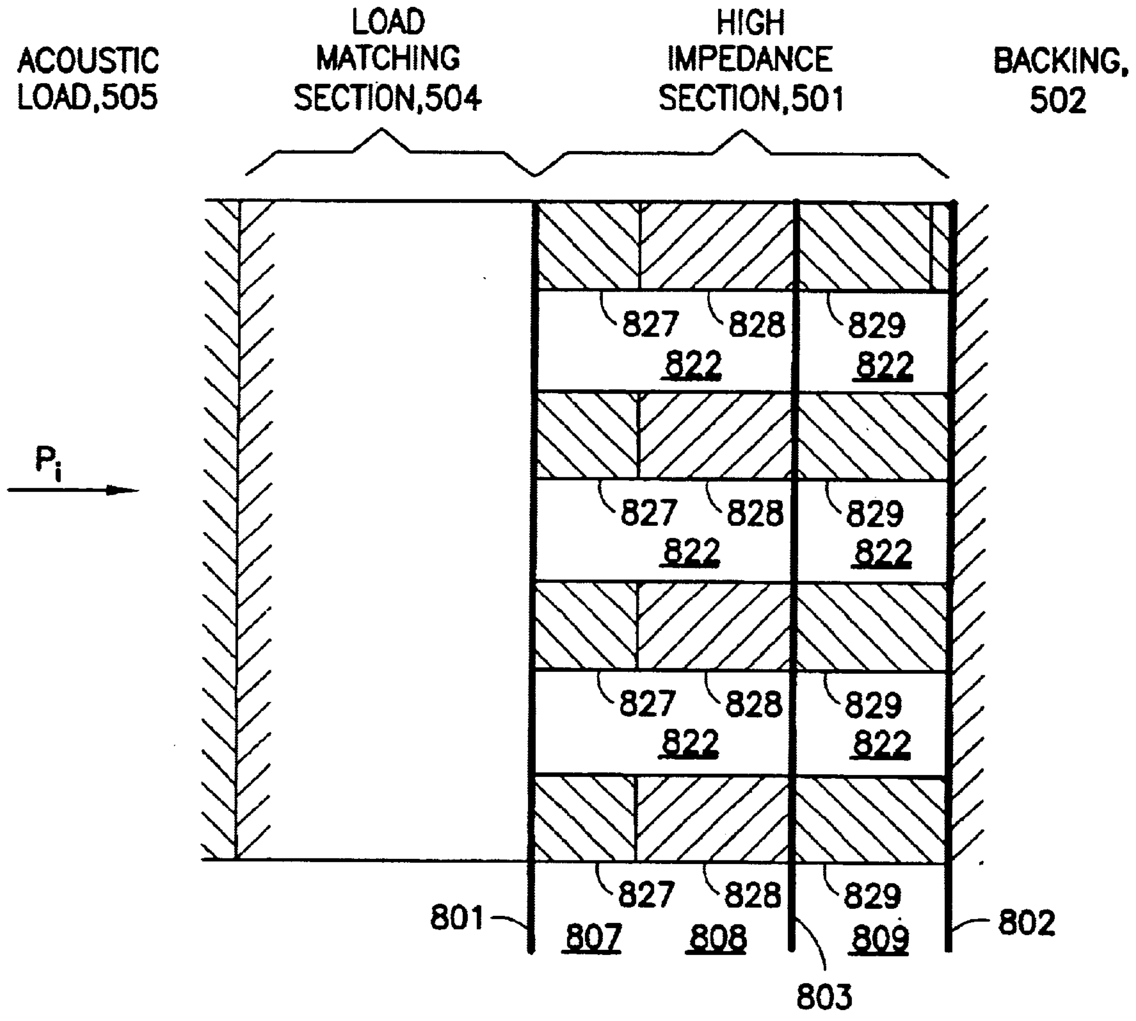
FIG. 8*b* and 8*c* shows examples of how both the piezoelectric layers, a high impedance elastic and a load matching elastic layers can be made as composites.

To analyze the frequency variation of $|H_{ele}|$ we use the electrode structure in the high impedance section as shown in FIG. 8*a* as an example. Three electrodes, 801, 802, 803, are placed within the general structure of FIG. 5, with a missing back matching section. The high impedance section contains a purely elastic layer 807 in front of the piezoelectric layers 808 and 809 that in this example have the same direction of polarization, indicated by the arrows P1 (831) and P2 (832). Electrode 801 is placed at the front of the piezoelectric layers, electrode 802 is placed at the back, while electrode 803 is placed in the middle of the piezoelectric section. According to the discussion above, the layer 807 can be made of a conducting material, for example Al, Mg or heavily doped Si, which hence can merge with the electrode 801. The layer 807 can also be an unloaded piezoelectric layer.

The three electrodes constitute three possible electric ports 804, 805, and 806. We note that Port I (804) can be viewed as a series coupling of Port II (805) and III (806), where the currents are the same in all ports while the voltages of Port II and III are added to give the voltage of Port I. One can also obtain a $4^{th}$ port by parallel coupling of Port II and III, where one in the structure of FIG. 8 then must separate the electrode 803 into two electrode layers with an electrically isolating layer of acoustically negligible thickness between. The left layer of 803 is galvanically coupled to electrode 802 and the right layer of 803 is galvanically coupled to electrode 801, so that the voltage is the same across all ports and the current of the parallel port is the sum of the currents in Port II and III.

Figure 7B:
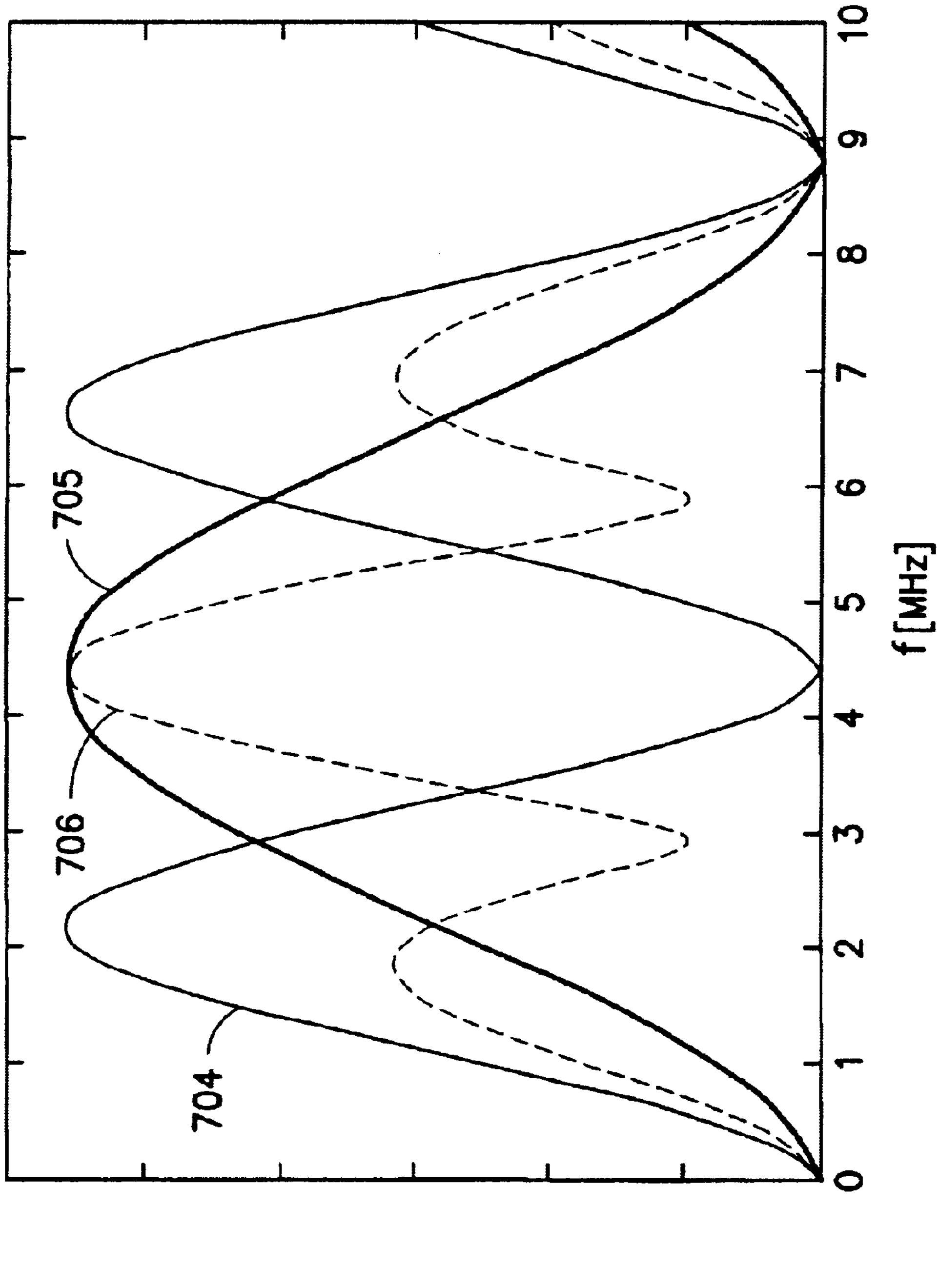
FIG. 7*b* shows the amplitude of the electrode transfer functions for three electrodes giving three electric ports as schematically shown in FIG. 8.
Figures 1, 12C:
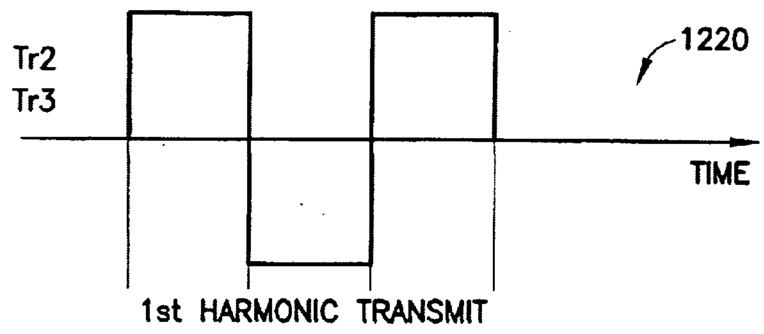
Figures 2, 12C:
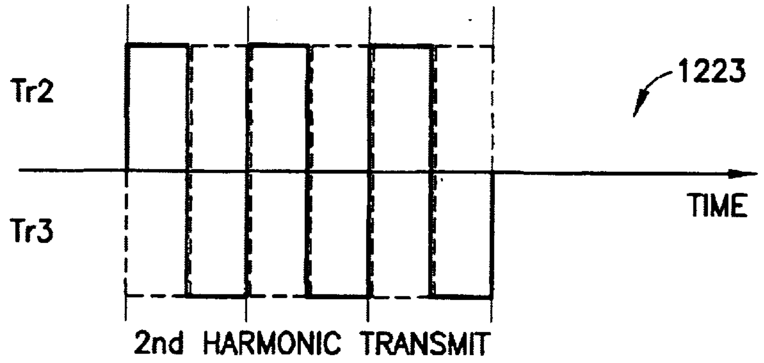
Figures 3, 12C:
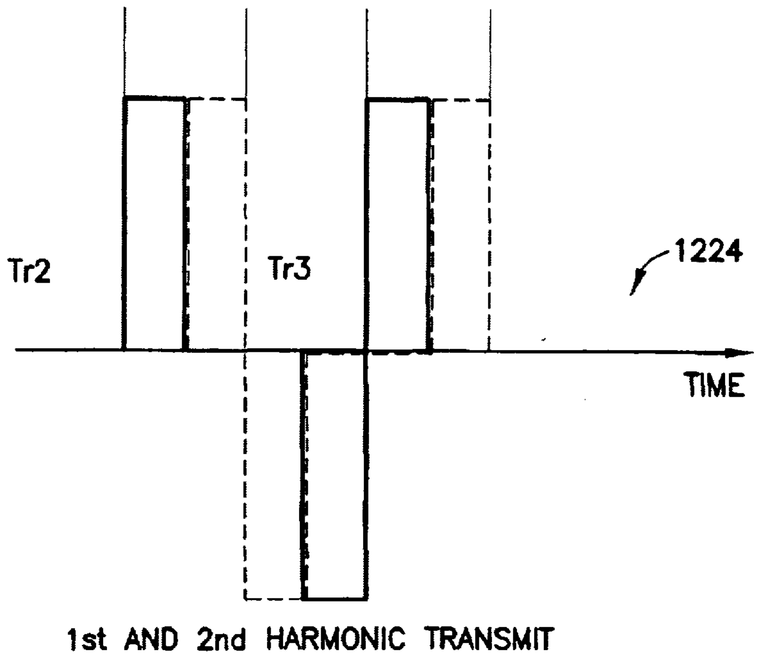

FIG. 7*b* shows $|H_{ele}|$ according to Eq.(21b) for the three electric ports in FIG. 8*a*. 704 shows $|H_{ele}|$ for Port I (804), while 705 shows $|H_{ele}|$ for Port II (805), and 706 shows $|H_{ele}|$ for Port III (806). With reference to FIG. 6 we note that the maximum of $|H_{ele}|$ is found when both electrodes are located at antinodes with opposite phases. The limited bandwidth of $|H_{ele}|$ is found because the antinodes move across the electrodes as the frequency varies. It is then clear from FIG. 6 that the electric ports which use the back electrode that is located at an antinode for all frequencies, gives the widest bandwidth of the main lobe of $|H_{ele}|$, where the bandwidth is limited by that the front antinode moves across the front electrode. For the front port, Port III shown as 806 in FIG. 8*a*, 706 shows a break-up of $|H_{ele}|$ into sublobes of less bandwidth because both the front and back antinodes move with frequency across the front and back electrodes. The sublobes can be useful for improved separation of the signal into separate frequency bands.

Figure 9:
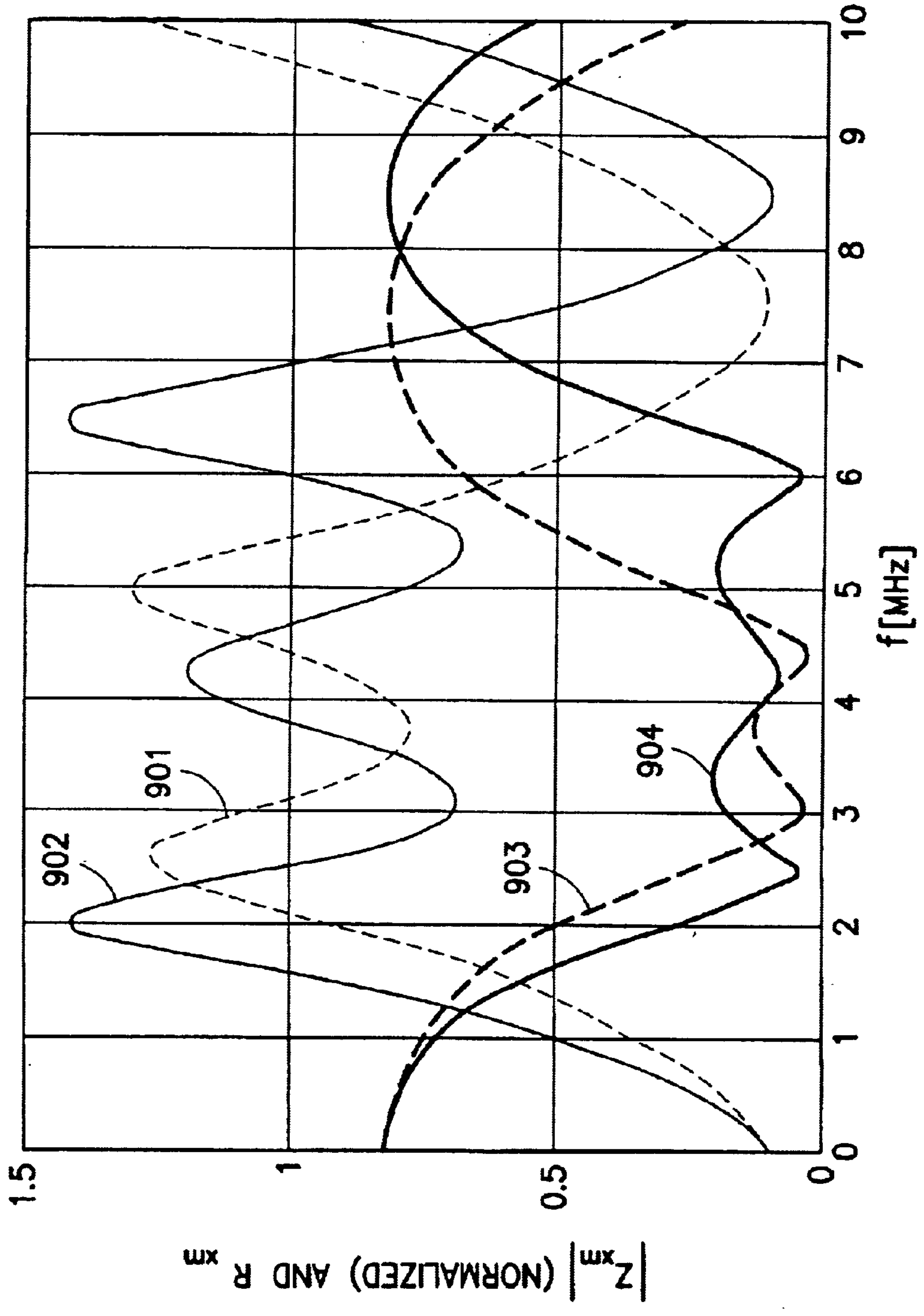
FIG. 9 shows the example impedances seen into the load matching section together with the reflection coefficients between the high impedance and the load matching section, for a 2-layer and a 3-layer matching.

Practical manufacturing requires that the load matching section is composed of a finite number of matching layers, typically 1–3. With a finite number of layers one can only get an approximation of $Z_{xm}$ to $Z_x$ in finite bands of frequencies, where 901, 902 in FIG. 9 shows $Z_{xm}/Z_x$ as a function of frequency for an example of 2 and 3 matching layers with thicknesses and characteristic impedances given in Table 1. We have assumed that the piezoelectric layers are made of a ceramic/polymer composite with characteristic impedance $Z_x$~17MRayl. The corresponding reflection coefficient seen from the high impedance section towards the load matching section, $|R_{xm}|$, is shown as 903 and 904 for the 2 and 3 layer matching, respectively. We note in FIG. 9 that $Z_{xm}$ becomes low at low frequencies, where the layer thicknesses become much thinner than λ/4, and at higher frequencies where the layer thicknesses each are close to a whole number of λ/2 thick. In these regions $|R_{xm}|$ becomes high as with no matching.

We note that the load impedance transformation is efficient in a band of frequencies where $Z_{xm}$~$Z_x$, where the reflection coefficient $R_{xm}$ in this example shows equal ripple performance obtained by Chebyshev matching. With this matching the characteristic impedances $Z_n$ of matching layers are symmetric in the following respect $$Z_n = \frac{Z_x Z_L}{Z_{N+1-n}} \quad n = 1, 2, \ldots, N \tag{24}$$

where n labels the matching layer number from the load material to the high impedance section, and N is the total number of matching layers. For two matching layers, one can choose $Z_1$, defining the ripple-level of the reflection coefficient $R_{xm}$, and Eq.(24) then gives the impedance of the other layer as $Z_2=Z_xZ_L/Z_1$. For an odd number of layers N, we get for the mid layer n=p=(N+1)/2 from Eq. (24) that $Z_p=\{Z_xZ_L\}^{1/2}$. With a 3-layer matching $Z_2=\{Z_xZ_L\}^{1/2}$ is given, and selecting $Z_1$ defines the ripple level of $R_{xm}$, while Eq.(24) gives $Z_3=Z_xZ_L/Z_1$.

The efficient load matching bandwidth increases with the number of layers N. With increasing N one can therefore reduce the thickness of the matching layers, while maintaining the low frequency performance of the matching. The upper limit of the efficient band hence moves proportionally upwards in frequency, while the low frequency performance of Port I and IV are maintained. In FIG. 9, the thickness of the 3-layer matching, 902, is minimized to obtain improved high frequency performance of Port II and Port III of FIG. 8*a*, while maintaining allowable ripple in the frequency responses of Port I and Port IV. For the two-layer matching, 901, we have traded some low frequency performance of Port I and IV of FIG. 8*a* compared to the three-layer matching, 902, to obtain better high frequency performance of Port II and Port III.

TABLE 1

Characteristic impedances and thicknesses of the matching layers

| | Zxm | Z1 MRayl | Z2 MRayl | Z3 MRayl | f, λx/2, MHz | f, λm/4, MHz |
|---|---|---|---|---|---|---|
| 2 Layer | 16.5 | 3.0 | 8.3 | | 4.38 | 2.8 |
| 3 Layer | 18.0 | 2.7 | 5.2 | 10.0 | 4.38 | 2.8 |

We note that the highest characteristic impedance of the 3-layer matching is 10MRayl, which is for example found for Mg and some glasses. The lowest characteristic impedance is 2.7 MRayl, which can be found with plastic materials. One can hence use homogeneous materials for these layers, while the 5.2MRayl impedance for the mid layer can be obtained with a mixture of polymer and tungsten powder.

Excitation of transversal modes and shear waves in metallic high impedance elastic layers and load and back matching layers, can introduce problems. In such situations, the invention devices a solution where these layers are made as metal/polymer composites. For the high impedance elastic layers one can attach layers of silver (Ag: $Z_0$~38MRayl), zink (Zn: $Z_0$~30MRayl), or zirconium (Zr: $Z_0$~30.1MRayl) directly to the uncut ferrolectric ceramic material. These materials have characteristic impedances that deviates ~10% and less from actual ferroelectric ceramic materials, introducing reflection coefficients at the interfaces that are ~5% and less. Layers of such materials hence define thickness vibrations in unity with the whole ceramic layers, and can be diced together with the ceramic layers, filling the dice grooves with polymer material to form the final composite material. An example of such a metal/polymer composite elastic layer is shown as 807 in FIG. 8*b*. The elastic layers of metal/polymer composites can then be used as part of the electrodes as the metallic slabs 827 connect directly to the ferroelectric ceramic slabs 828. The metalic slabs are then connected to a complete electrode by the metal layer 801. Other actual materials for elastic conducting layers to adhere on the ceramic layer before dicing to the composite, are alloys like brass ($Z_0$~36MRayl) or cast iron ($Z_0$~33MRayl).

Figure 8C:
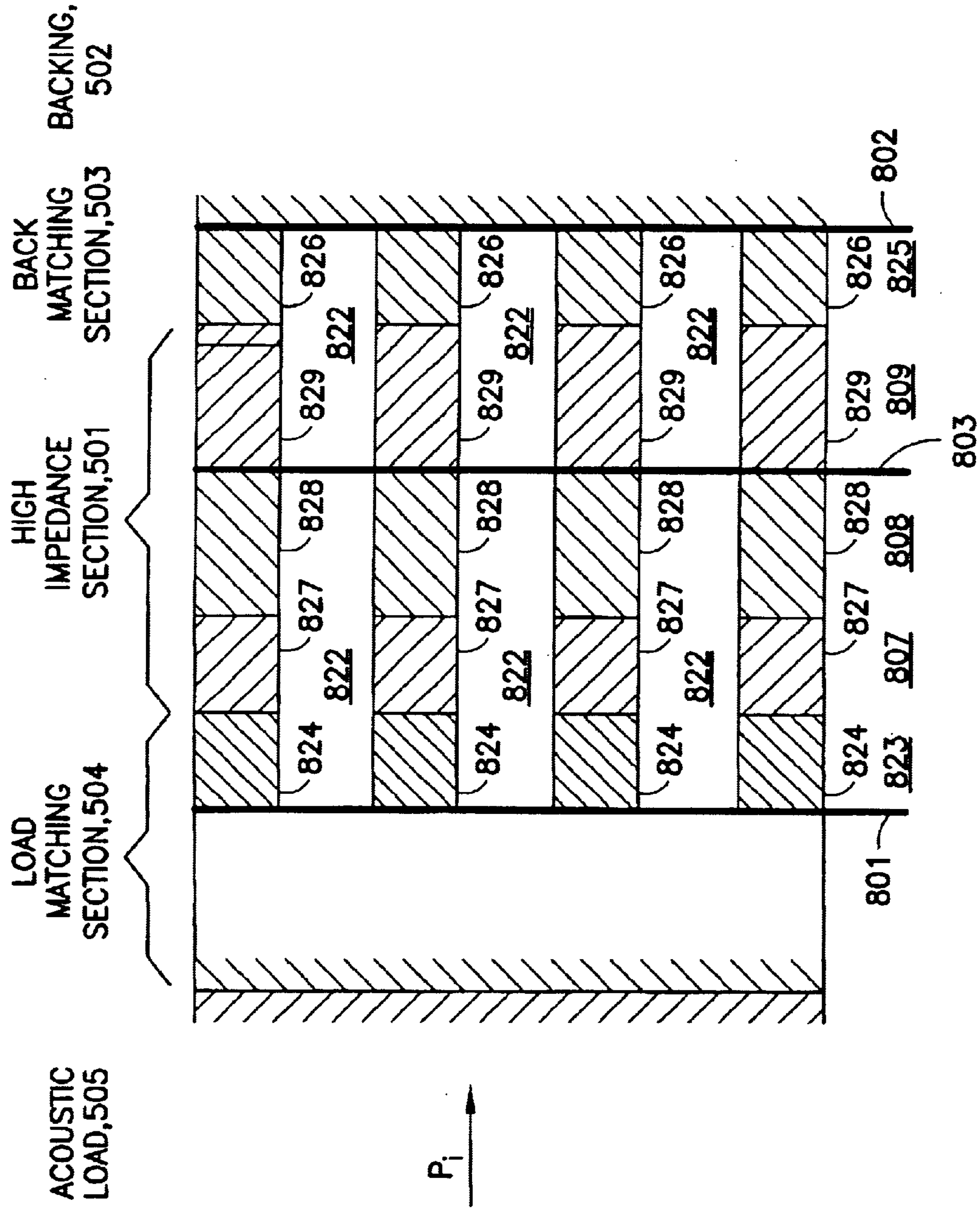

To avoid transversal resonance modes in metal load and back matching layers, the invention devices the use of metal/polymer matching layers as illustrated in FIG. 8*c*, where 823 exemplifies a load matching layer and 825 exemplifies a back matching layer. The whole metal electrodes are plated onto the whole ceramic before the dicing for the composite manufacturing. Examples of useful materials both for the load and back matching, are aluminum (Al: $Z_0$~17.5MRayl), highly doped silicon (Si: $Z_0$~19.5MRayl), titanium (Ti: $Z_0$~24MRayl), or magnesium (Mg: $Z_0$~10MRayl), while for the back matching it can also be useful to use metal layers with higher characteristic impedances, like silver (Ag: $Z_0$~38MRayl), gold (Au: $Z_0$~62.5MRayl), platinum (Pt: $Z_0$~85MRayl), or tungsten (W: $Z_0$~103MRayl). All the layers are then diced together and the dice kerfs filled with polymer, so that a multilayer composite is formed, with characteristic impedances of the composite layers approximating the required impedances of both the high impedance section and the matching layers.

The metal/polymer composites functions as electrodes for the piezoelectric composites by connecting the metal posts 824/827 with a continuous metal film 801 for the front electrode and the metal posts 826 with the continuous layer 802 for the back electrode. As the electrode 803 is continuous for all posts in the transducer, the composite layers 808, 807, and 823 must be manufactured as one unit, while the layers 809 and 825 are manufactured as a separate unit. After the dicing and polymer filling, an electrode 803 is adhered on the back of layer 808 and the front of layer 809, and the units are merged together, for example so that the dual electrodes 803 forms electric contact.

The metallic layers can for example be applied by electroplating on a thin, sputtered base metallic layer on the ceramic, followed by further electroplating of other metals. As the plating is done before dicing and application of polymer, the materials tolerate high temperatures that are required for some of the electrolytic baths (e.g. ~450° C. for Mg). The thickness of the metal posts can be further tuned after the dicing by for example etching to reduce the thickness or electroplating to increase the thickness, to tune the volume fill and hence the characteristic impedance of the resultant metal/polymer layer. The post thicknesses can also be individually tuned by limited depth dicing with different thickness of the saw blades, making it possible to reduce both the ceramic post and the metal post thicknesses relative to each other. This opens for the use of metal layers with characteristic impedance with larger deviations from the ceramic materials. Examples with relatively reduced thickness of the metallic posts are copper (Cu: $Z_0$~44.3MRayl). With relatively increased thickness of the metallic posts (also counting reduced thickness of the ceramic posts) one can use titanium (Ti: $Z_0$~27MRayl), germanium (Ge: $Z_0$~27MRayl), gallium arsenide (GaAs: $Z_0$~26MRayl), or tin (Sn: $Z_0$~24.5MRayl).

Variable volume fill of the different layers can also be obtained with a first dicing of the piezoelectric layer 808 with large distance between the dicing grooves and filling the grooves with polymer. The elastic layer 807 is then adhered on the coarse piezoelectric/polymer composite as a continuous layer, and the combined piezoelectric and elastic layers are further diced between the 1st grooves, so that a denser dicing of the piezoelectric than the elastic layer is obtained. The matching layer 823 can then be adhered to the resulting composite and a final dicing of the combined piezoelectric, elastic, and matching layers can then be done between the 1st and 2nd grooves, so that the piezoelectric layer obtains the densest dicing, the matching layer the 2nd densest dicing, and the matching layer obtain the least densest dicing. One should note that adhering both the elastic layer and the matching layers before the 2nd dicing, these layers gets the same volume fill. One should also note that dicing in the reverse order, i.e. starting with matching layer and adhering the elastic and the piezoelectric layer, one can get the lowest volume fill of the matching layer, with equal or larger volume fill of the elastic layer, with equal or larger volume fill of the piezoelectric layers.

Figure 6B:
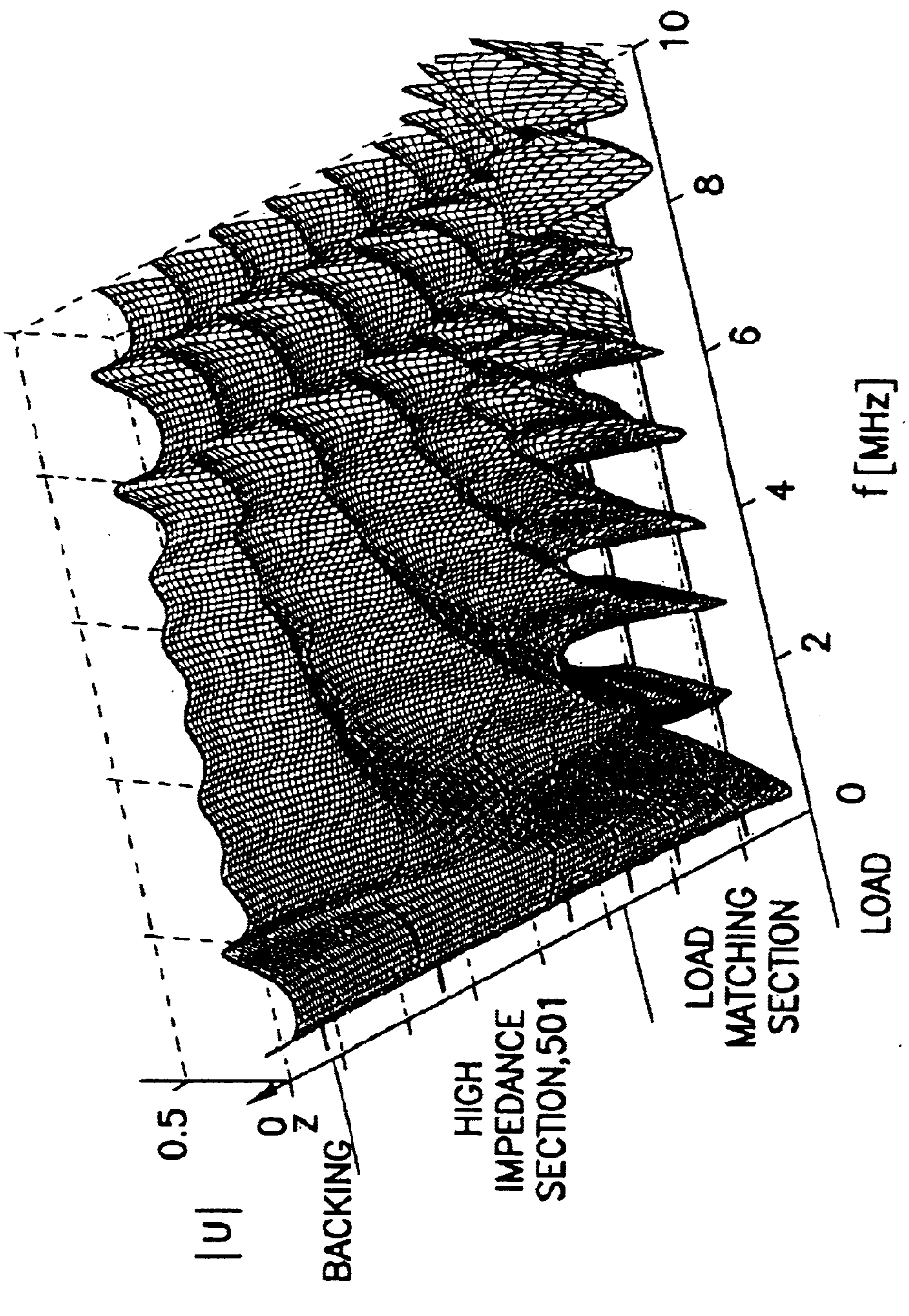
FIG. 6*b* shows the amplitude for a practical matching between the load and the high impedance section.

The standing wave pattern of $|U_n(z,\omega)|$ for the transducer with the 3-layer matching is shown in FIG. 6*b*, where we note that the backing interface is still found at an antinode for all frequencies because the reflection coefficient at this interface is real and unmodified by the less ideal matching at the load interface. With low absorption, $|H_{stru}(\omega)|$ as defined in Eq.(21c) is therefore approximated as $|U_n(z,\omega)|$ at the back interface, and is illustrated as the curve 702 in FIG. 7*a*, which also shows the reflection coefficient $|R_{xm}|$ as 904 for comparison. We note that $|H_{stru}(\omega)|$ now is frequency dependent due to the limited efficient bandwidth of the load matching.

By proper adjustment of the total thickness $L_x$ of the high impedance section, one obtains thickness resonances in the high impedance section at the low and high ends of the efficient load matching band, where $Z_{xm}$ reduces below $Z_x$. The requirement for resonances is that the sum of the roundtrip propagation phase ($2kL_x$) in the high impedance section and the phases of the reflection coefficients at the load and back interfaces of the high impedance section, is a whole number of $2\pi$.

This requirement is satisfied where the matching layers become close to an even number of $\lambda/2$ thick (including $0*\lambda/2$) at 703 below the effective impedance transformation band, and at 704 above the first effective impedance transformation band (between $0*\lambda/2$ and $\lambda/2$). The resonance at 705 is found where the thicknesses of both the load matching section and the high impedance section are close to an even number of $\lambda/2$, and hence is sensitive to the selected thickness of the load matching layers, as these can be adjusted somewhat with minor changes in the transfer functions in the efficient transduction band.

The resonances slightly below and above the first effective band of the load matching, extend the effective bandwidth of $|H_{stru}|$ outside the effective band of the load matching section. Increasing $L_x$ by the added layer 807 of FIG. 8*a*, reduces the resonance frequency of 703 and increases the resonance frequency of 704, so that the total band of $|H_{stru}|$ is increased by the layer. This is demonstrated by the curve 706 in FIG. 7*a* which shows $|H_{stru}|$ without the added layer 807.

The resonances at 703, 704 are hence determined by the total thickness of the high impedance section, $L_x$. Manipulation of the thickness of the piezoelectric layers while $L_x$ is kept constant by adjusting the thickness of the added elastic layer 807, allows further tuning of $|H_{ele}|$, while $|H_{stru}|$ with unloaded electric ports is unchanged. This can for example be useful to obtain adequate high frequency operation of $|H_{ele}|$, by reducing the thickness of the piezoelectric layers, adjusting the thickness of 807 for constant $L_x$.

Figure 10A:
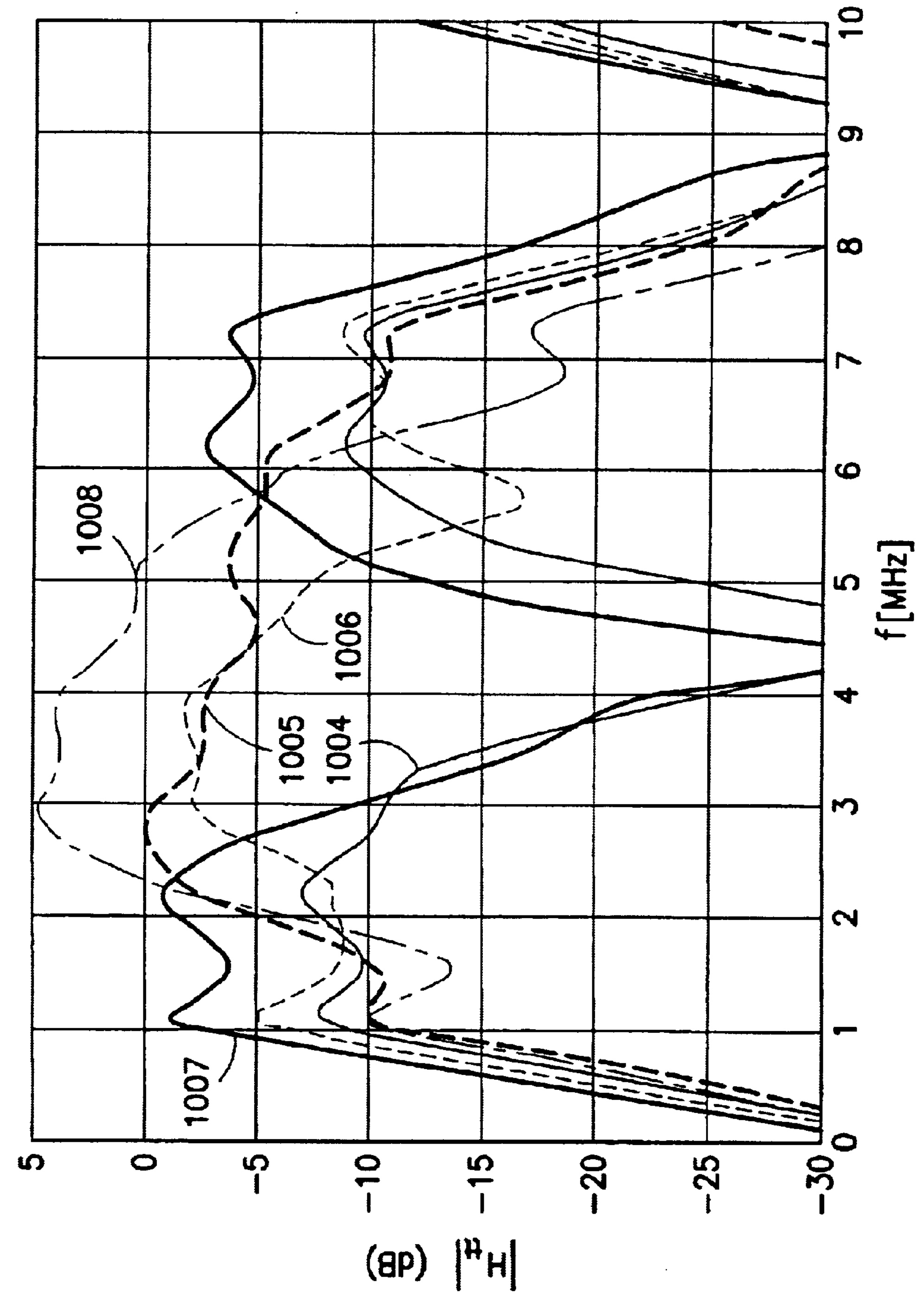
FIG. 10*a* shows the transfer functions for a 3-layer matching and FIG. 10*b* shows the transfer functions for a 2-layer matching.

The transmit transfer functions, $H_{tt}(\omega)$, of the ports in FIG. 8*a* with the 3-layer matching are shown in FIG. 10*a*, where 1004 shows $|H_{tt}(\omega)|$ for Port I (804), 1005 shows $|H_{tt}(\omega)|$ for Port II (805), and 1006 shows $|H_{tt}(\omega)|$ for Port III (806) of FIG. 8. 1007 shows the $|H_{tt}(\omega)|$ that is obtained by coupling layer I and II in parallel, referred to as Port IV above. From Eq.(8) we see that $|H_{tt}(\omega)|$ describes the transmit transfer function for a voltage driven transducer. The strong transmit attenuation of Port I and port IV around 4.5 MHz, makes these ports well adapted for $2^{nd}$ to $4^{th}$ harmonic measurements, as discussed below.

Figure 10B:
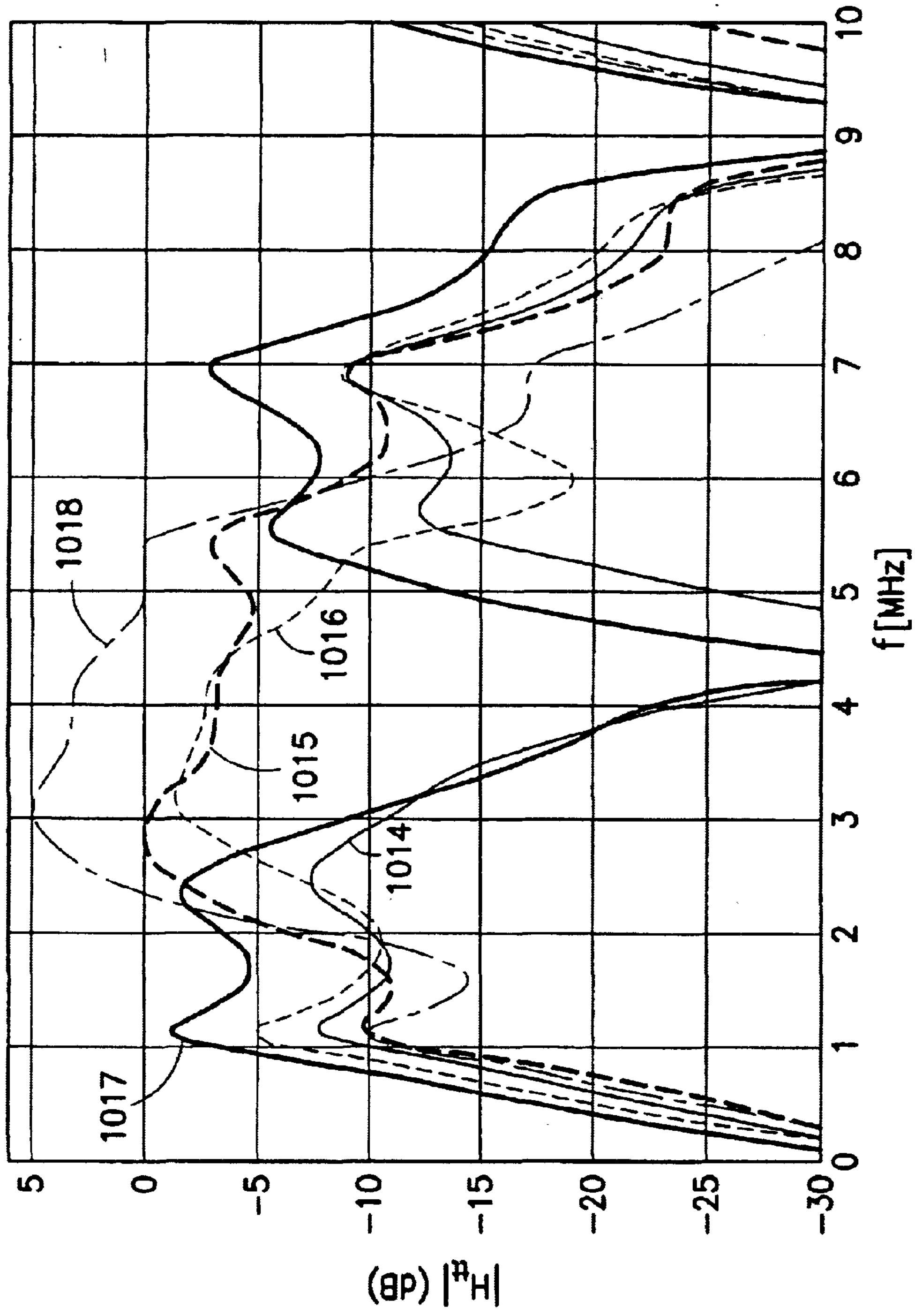

The transmit transfer functions, $H_{tt}(\omega)$, of the ports in FIG. 8*a* with the 2-layer matching are shown in FIG. 10*b*, where 1014 shows $|H_{tt}(\omega)|$ for Port I (804), 1015 shows $|H_{tt}(\omega)|$ for Port II (805), and 1016 shows $|H_{tt}(\omega)|$ for Port III (806) of FIG. 8. 1017 shows the $|H_{tt}(\omega)|$ for Port IV. The properties of the transfer functions are similar to those in FIG. 10*a*, except that the 2-layer matching gives poorer high frequency performance for Port II (1015) and increased low frequency ripple of Port I (1014) and Port IV (1017), due to the lower efficient bandwidth of $H_{stru}$ with the 2-layer matching described with reference to FIG. 9.

Figure 8D:
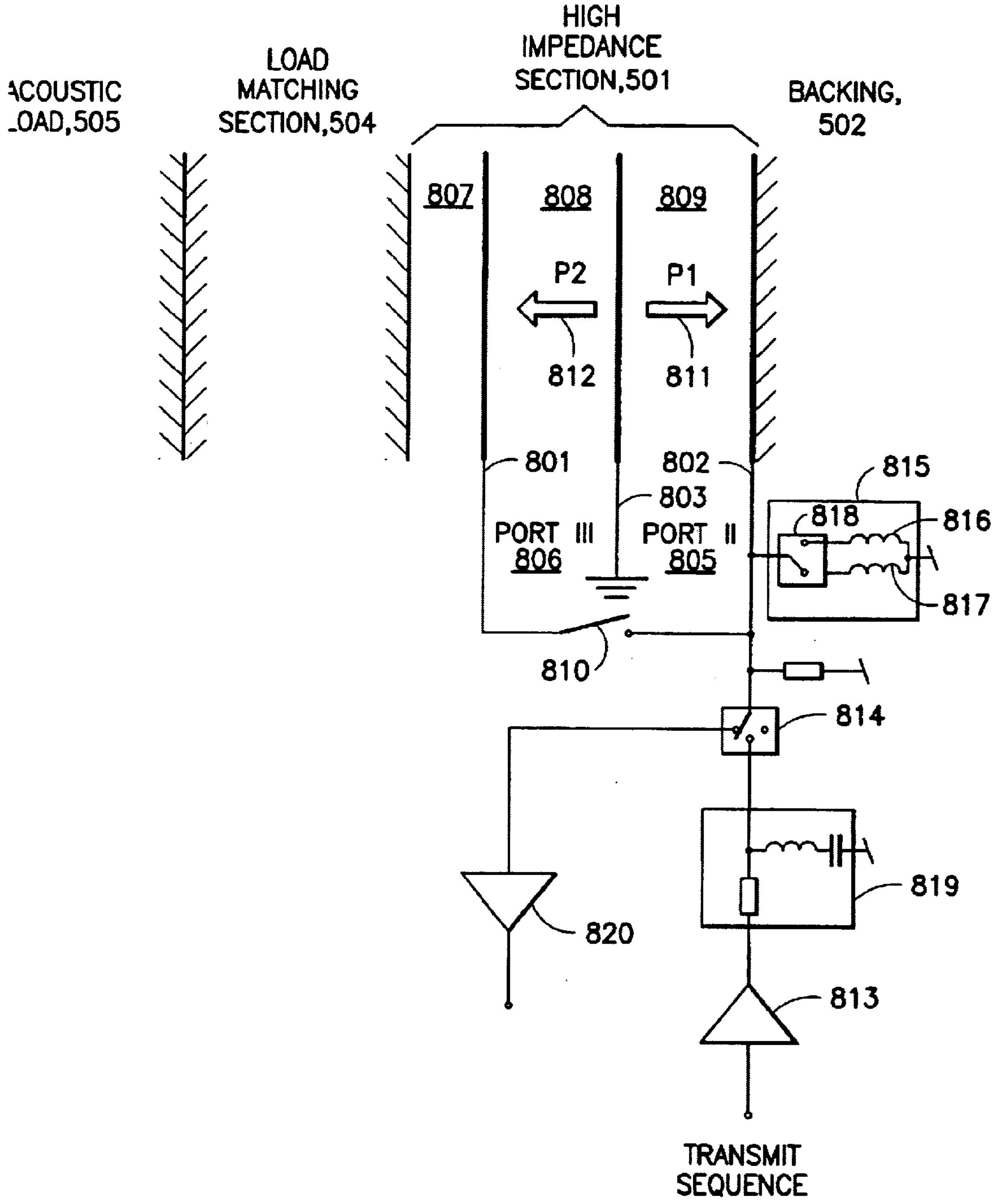
FIG. 8*d* shows a transceiver system for electronic switching between electric ports.

At transmit, one can obtain parallel coupling of Port II and Port III in FIG. 8*a* by driving Port II with a voltage signal v(t), and Port I with a voltage signal 2v(t). Combined designs that allows electronic selection of transfer functions of FIG. 10*a* and 10*b*, are shown in FIGS. 8*d* and 12*a*, where the high impedance section is composed of the same layers 807, 808, 809 and the same electrodes 801, 802, 803, as in FIG. 8*a*. The two piezoelectric layers are given opposite polarization P1 and P2 indicated by the arrows 811 and 812. One should note that the polarization directions could be changed in both layers, as long as they are opposite in the two layers.

Grounding of the middle electrode 803 and coupling electrodes 801 and 802 galvanically together through the switch 810 and transmitting with a voltage amplifier 813 that is connected to the electrodes through the transmit/receive switch 814, gives a transmit parallel coupling of Port II and Port III, denoted Port IV with the transmit transfer function $|H_{tt}(\omega)|$ given as 1007 in FIG. 10*a* or 1017 in FIG. 10*b*. The circuitry 815 in FIG. 8*d*, can be used to tune the negative phase angle of the electric port input impedances, according to well known methods. In the Figure one have illustrated two electric inductors 816 and 817 that can be selected with the switch 818 so that one can use selectable coils when 810 is open or closed, to tune the electric impedance of Port II and Port IV selectively. The series tuned LC-filter circuit 819 can for example be used to attenuate harmonic components, like $2^{nd}$ or $3^{rd}$ components, in the transmitted signal to reduce interference with harmonic components generated in the tissue or possible contrast agent bubbles. The resonance frequency of this circuit is conveniently placed at the low values of 1007 or 1017 around 4.5 MHz for combined attenuation of the transmitted harmonic components.

Figure 11A:
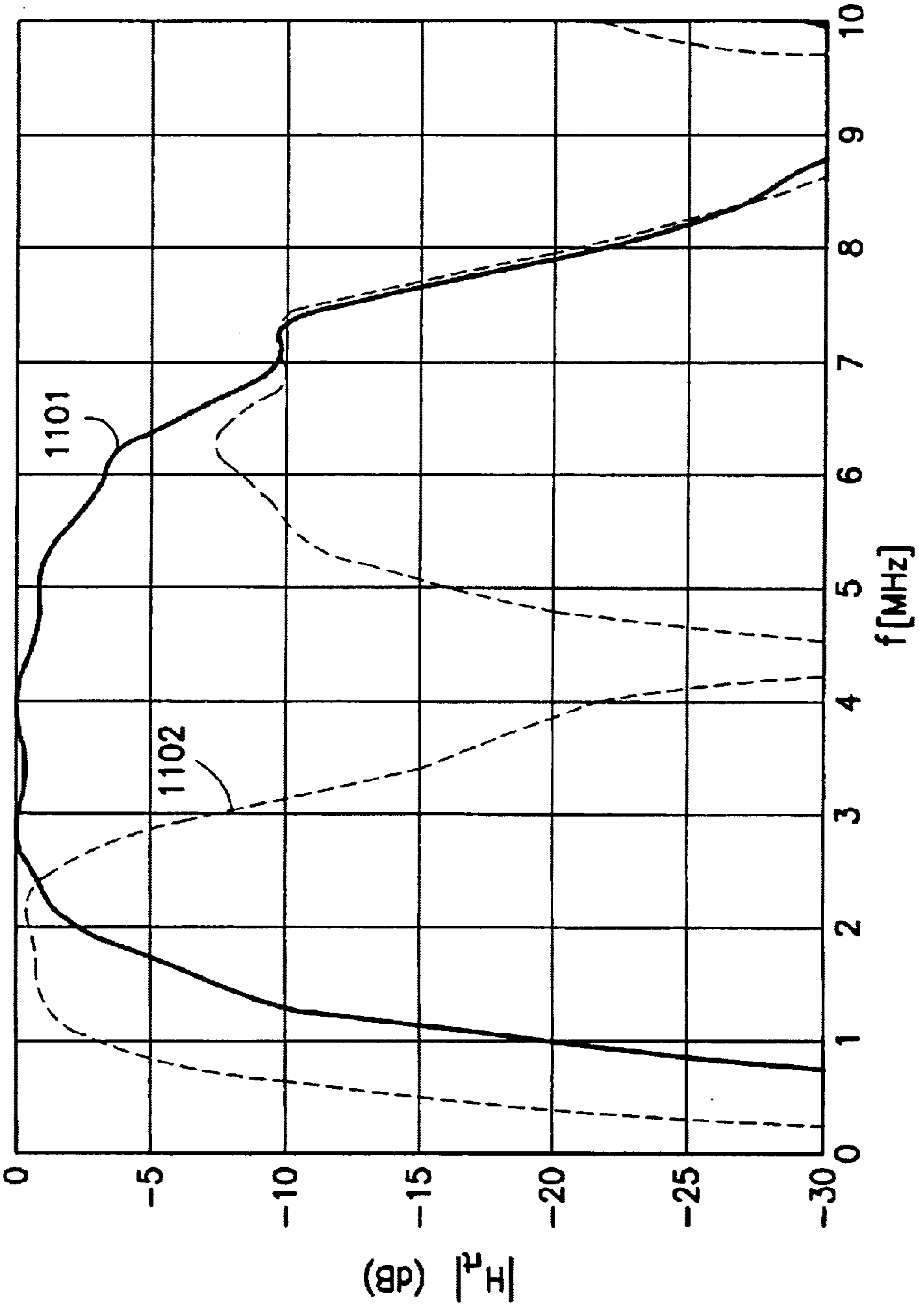

In receive mode, the transmit/receive switch 814 in FIG. 8*d* is set to connect the receiver amplifier 820 to the electrodes. When the switch 810 is open, the receiver amplifier is picking up signal from Port II, which operates at higher frequencies than the parallel coupled port, to receive harmonic components of the transmitted frequency band, like $2^{nd}$, $3^{rd}$ or $4^{th}$ harmonic components. The switch 810 can hence be used to selectively access the parallel coupled Port IV, and Port II, both at transmit and receive. The receive transfer functions with selected receiver impedance (Ref. Eq.(10)) for Port II and Port IV are given as 1101 and 1102 in FIG. 11*a*. The electric transducer ports are tuned with the inductors 816 for Port II and 817 for Port IV of FIG. 8*d*.

The combined results of FIGS. 10*a*/10*b* and 11*a*, shows that the parallel coupled Port IV allows for both transmission and reception of ultrasound pulses in a low frequency band of 0.8–2.8 MHz, while Port II allows for both transmission and reception of ultrasound pulses in a higher frequency band 1.8–6.5 MHz. In particular we note that Port IV can be used to transmit a $1^{st}$ harmonic band of frequencies, while Port II can be used to receive $2^{nd}$, $3^{rd}$, or even $4^{th}$ harmonic components of the transmitted band, switching 810, 818, and 814 between transmission and reception.

It is often possible to make electric drive pulses that are low in $2^{nd}$ and $4^{th}$ harmonic components, while the $3^{rd}$ harmonic content is difficult to suppress. We note that the transmit transfer functions of Port I (1004, 1014) and Port IV (1007, 1017) shows low values around 4.5 MHz. Transmit of a $1^{st}$ harmonic pulse centered at ~1.5 MHz through these ports hence attenuates the $3^{rd}$ harmonic component in the transmitted acoustic pulse. Backscattered 1st harmonic components are then conveniently received through Port I or Port IV, and $2^{nd}$, $3^{rd}$, and $4^{th}$ harmonic components through Port II. The $|H_{tt}(\omega)|$ of Port II (1005, 1015) and of Port III (1006, 1016) are useful for transmitting a pulse with frequencies in a $2^{nd}$ harmonic band centered at ~2*1.5 MHz=3 MHz.

To maximally attenuate the transmitted harmonic components in the receive frequency band, one can transmit a pulse with frequencies in a $1^{st}$ harmonic band centered ~4.5/2=2.25 MHz ($2^{nd}$ harmonic measurements), ~4.5/3=1.5 MHz ($3^{rd}$ harmonic measurements), and ~4.5/4=1.13 MHz ($4^{th}$ harmonic measurements), and receive the harmonic bands around 4.5 MHz at Port II. Through adjustments of layer thicknesses as described above, the attenuation band can be placed at other frequencies.

FIG. 12*a* shows an arrangement where electronic switching of the layer coupling can be achieved with the transducer structure shown in FIG. 8*d*, with a larger flexibility than in FIG. 8*d*. A set of transmitter voltage amplifiers 1201 and 1202 drives the electrodes 802 and 801 through a set of electronically controlled switches 1203 and 1204, and coaxial cables 1205 and 1206, while electrode 803 is grounded. For improved efficiency of the transmitter amplifiers one could also use electric impedance matching networks between the transmitter amplifiers and the transducer ports illustrated as 1209 and 1210, according to known principles. The Figure illustrates parallel tuning coils where two coils can be selected for each port, depending on the operating frequency range. Other types of electrical matching is also highly actual, for example series tuning coils, or networks of coils and capacitors. To attenuate harmonic components in the transmit sequences, the Figure illustrates the use of added notch filters 1213 and 1214 on the transmit amplifiers.

Driving the transmitter amplifiers with the sequences Tr2=Tr3 as given in 1220 of FIG. 12*b*, one gets the transmit parallel coupled transfer function $|H_{tt}(\omega)|$ in 1007 of FIG. 10*a* or 1017 in Figure 10*b*, without galvanic coupling of electrodes 801 and 802. Such selection of Tr2 and Tr3 hence allows transmit of a band of frequencies around ~1.5 MHz. Driving the transmitter amplifiers with the sequence Tr2 of 1221 while the signal Tr3 is zero, one can transmit a band of frequencies around ~3 MHz according to $|H_{tt}(\omega)|$ of 1005 in FIG. 10*a* or 1015 in FIG. 10*b*. Similarly, exchanging the sequences of Tr2 and Tr3 in 1221, i.e. Tr2 is zero, while Tr3 represents a signal, one can transmit a band of frequencies around ~3 MHz according to $|H_{tt}(\omega)|$ of 1006 in FIG. 10*a* or 1016 in FIG. 10*b*.

Summing the drive signals Tr2 and Tr3 from 1220 and 1221, one will transmit a first harmonic band according to $|H_{tt}(\omega)|$ of 1007 or 1017, simultaneous with a $2^{nd}$ harmonic band of frequencies according to $|H_{tt}(\omega)|$ of 1008 or 1018 in FIGS. 10*a* and 10*b*. The resultant drive signals Tr2 and Tr3 are shown as 1222 in FIG. 12*b*, which are simple three level signals that can be generated with transistor switches.

The transmitted power around ~3 MHz can be increased by an anti-parallel coupling of Port II and Port III of FIGS. 8*d* and 12*a*. For the particular electrical polarizations of the layers shown in FIG. 12*a*, one gets an anti-parallel coupling of the electric ports by driving Tr2 and Tr3 with opposite polarities, i.e. Tr3=−Tr2 illustrated as 1223 in FIG. 12*c*. This gives transmit transfer functions $|H_{tt}(\omega)|$ illustrated as 1008 and 1018 in FIGS. 10*a* and *b*, which is efficient for transmitting a band of frequencies around ~3 MHz with ~6 dB higher amplitude than through Port II and Port III alone. Transmission of a combined $1^{st}$ harmonic and $2^{nd}$ harmonic pulse at ~1.5 MHz and ~3 MHz, respectively, is obtained by summing the drive signals Tr2 and Tr3 of 1220 and 1223, that gives the drive signals Tr2 and Tr3 of 1224 of FIG. 12*c*. One could also obtain an anti-serial coupling of Port II and Port III of FIGS. 8*d* and 12*a* by driving the ports with opposite voltage polarity, and disconnecting electrode 803 from ground, so that the currents in the two ports have opposite polarity, related to the polarization directions of layers 808 and 809. Similarly one obtains anti-series coupling of Port II and Port III by current driving electrodes 801 and 802 with opposite polarity, while electrode 803 grounded. This anti-serial coupling provides a similar transmit transfer function as 1008 and 1018 with ~6 dB less amplitude. Due to the decoupling of the electrode 803 from ground, this coupling is less desirable to use.

Figures 1, 12D:
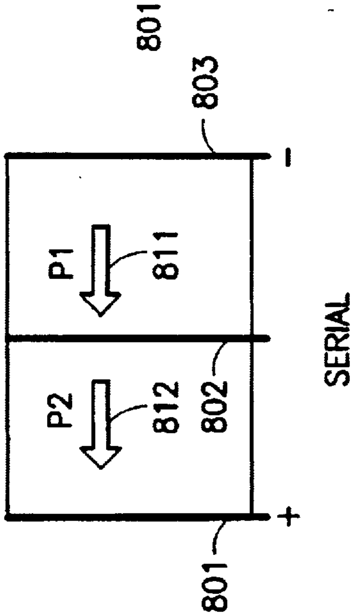
FIG. 12*d* shows examples of drive voltage polarity combined with different polarizations of the piezoelectric layers to form serial, anti-serial, parallel and anti-parallel coupling of the electric ports.
Figures 2, 12D:
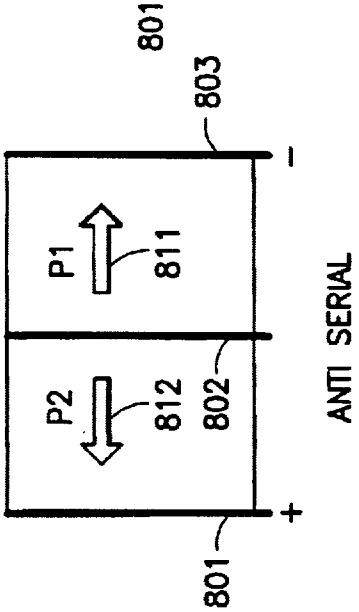
Figures 3, 12D:
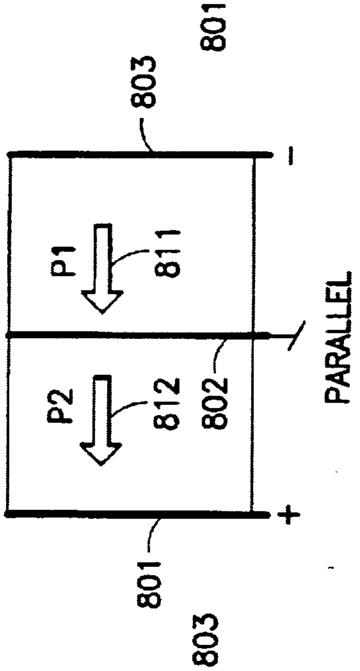
Figures 4, 12D:
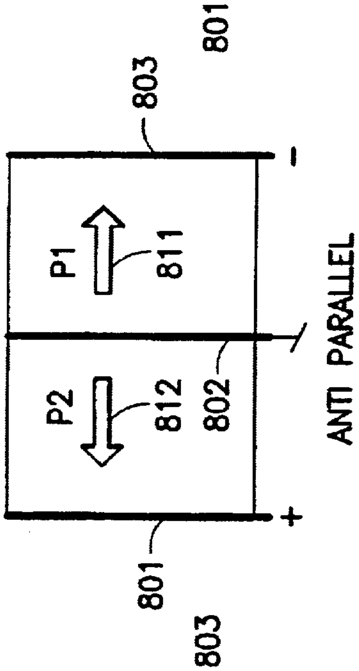
Figures 5, 12D:
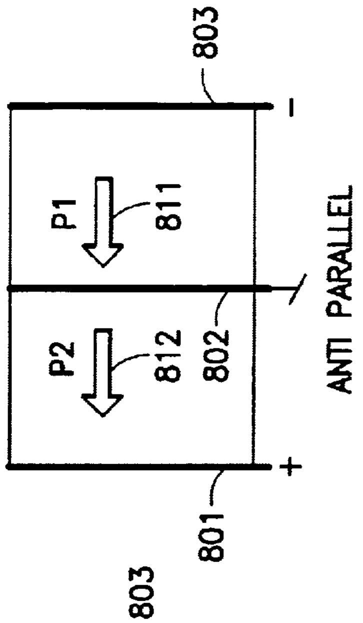
Figures 6, 12D:
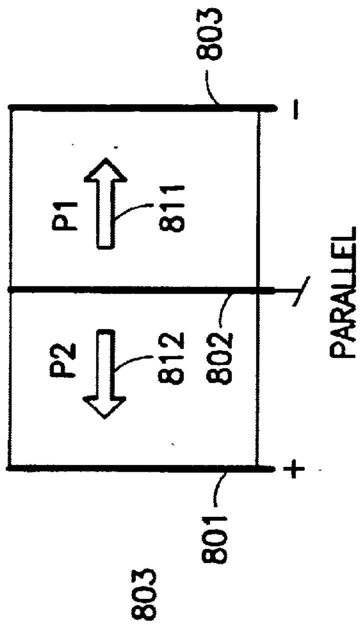
FIG. 6 shows the standing wave pattern of the amplitude of the vibration velocity, where

FIG. 12*d* shows an overview of the type of transmit couplings that can be obtained with the structure in FIG. 12*a*, using various polarizations of the piezoelectric materials with related polarities of the drive voltages. For the serial and anti-serial couplings the electrode 802 must be free floating. The electrical serial coupling of two ports is defined by that the currents into the two electric ports are equal and the voltages are summed, while the electrical anti-serial coupling is defined by that the currents have opposite direction and equal magnitude and the voltages are subtracted. The polarity of both the current and the voltage is related the direction of the piezoelectric polarization. The parallel coupling is defined by that the voltages are the same for each electric port while the currents are added, while the electrical anti-parallel coupling is defined by that the voltages have opposite polarity and equal magnitude and currents are subtracted. One should note that the function is preserved if both polarity directions of the piezoelectric materials are changed opposite to what is shown in the Figure, or similarly the polarity of the voltages are changed opposite to what is shown in the Figure.

Hence the transmitter/transducer structure of FIG. 12*a* is highly suited for transmitting pulses selectively in a 1st and a $2^{nd}$ band of frequencies, or transmission of a pulse with frequencies both in a $1^{st}$ and a $2^{nd}$ harmonic band. Both Port II and Port III can also be used to transmit in a $3^{rd}$ band of frequencies, and the structure can be used to simultaneously transmit pulses with frequencies that do not have a harmonic relation to each other.

In receive mode, the switches 1203 and 1204 are set to connect the electrodes 801 and 802 via the coaxial cables 1205 and 1206 to the receiver amplifiers 1207 and 1208. To improve sensitivity and receive transfer functions, the switches 1211 and 1212 of the impedance matching networks 1209 and 1210 are set for optimal receiver function in the selected bands.

Figure 11B:
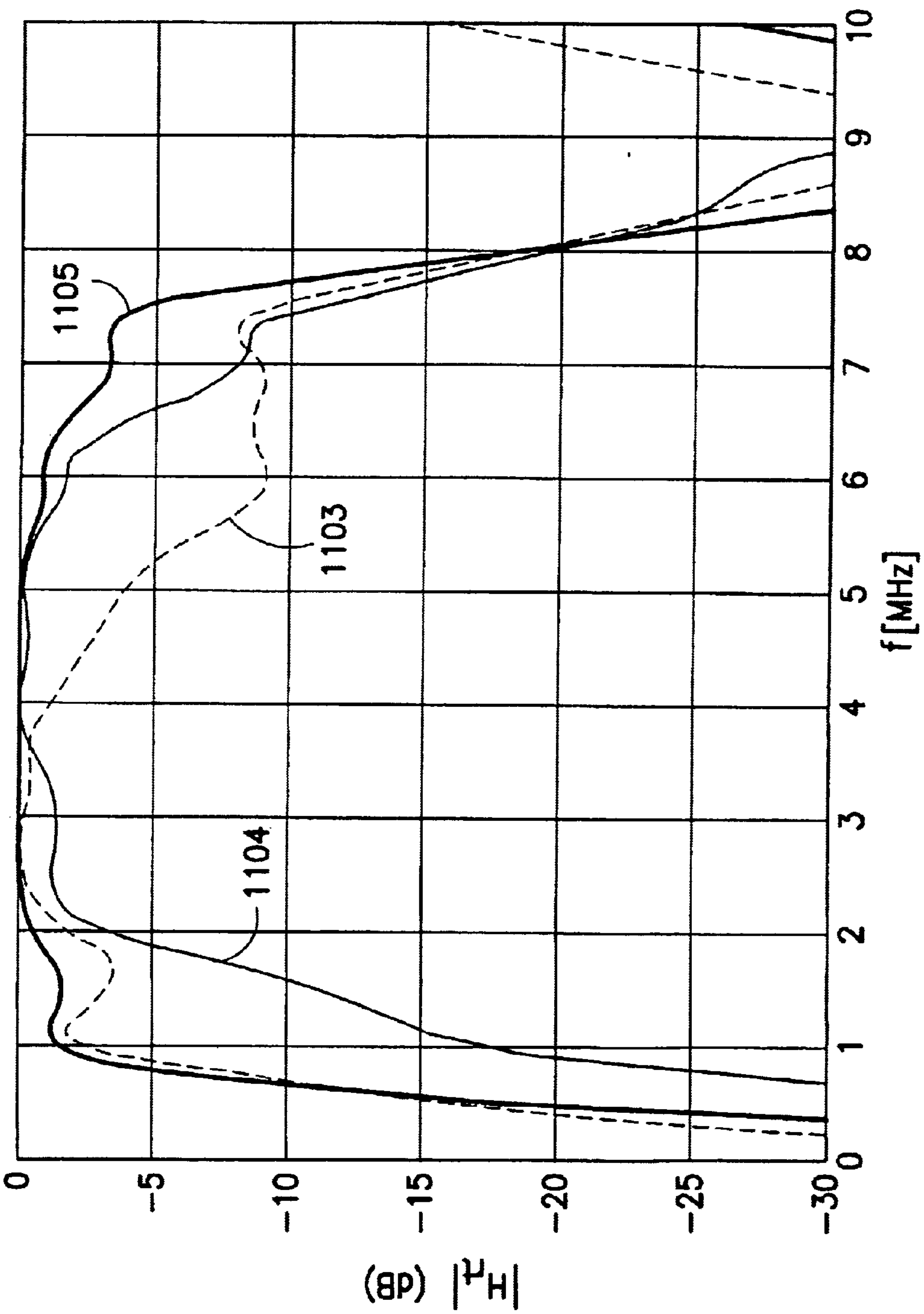
FIG. 11*b* shows transfer functions obtained with the transceiver structure in FIG. 12*a;*

Typical receive transfer functions $|H_{rt}(\omega)|$ of the two layers with tuned electrical loading, are shown in FIG. 11*b*, where 1103 shows the $|H_{rt3}(\omega)|$ for electrode 801, and 1104 shows the $|H_{rt2}(\omega)|$ for electrode 802. Relating to a $1^{st}$ harmonic transmitted band centered at 1.5 MHz (1007/1017 of FIGS. 10*a*/*b*)), we see that electrode 801 efficiently receives signals with frequency components in both the $1^{st}$, $2^{nd}$, and $3^{rd}$ harmonic frequency bands, while electrode 802 efficiently receives signals with frequency components in the $2^{nd}$, $3^{rd}$, and $4^{th}$ harmonic frequency bands of the transmitted pulse. Hence the structure is able to both transmit and receive frequencies over 2 octaves.

The outputs of the receiver amplifiers can conveniently be combined in the Filter and combination unit 1215 to improve the receiver transfer functions for example by a combined filtering that gives $$V_c(\omega)=H_{c2}(\omega)V_{r2}(\omega)+H_{c3}(\omega)V_{r3}(\omega) \tag{24}$$

where $V_{r2}(\omega)$ is the output of receiver amplifier 1207 and $V_{r3}(\omega)$ is the output of receiver amplifier 1208. Possible filters are the (m,N) filters $$H_{c2}(\omega) = \frac{|H_{rt2}(\omega)|^{m-2} H_{rt2}^{*}(\omega)}{|H_{rt2}(\omega)|^{m} + |H_{rt3}(\omega)|^{m} + \max_{\omega}\{|H_{rt2}(\omega)|^{m} + |H_{rt3}(\omega)|^{m}\}/N} \quad (25)$$

$$H_{c3}(\omega) = \frac{|H_{rt3}(\omega)|^{m-2} H_{rt3}^{*}(\omega)}{|H_{rt2}(\omega)|^{m} + |H_{rt3}(\omega)|^{m} + \max_{\omega}\{|H_{rt2}(\omega)|^{m} + |H_{rt3}(\omega)|^{m}\}/N}$$

The full receive transfer function of this combination is $$H_c(\omega) = H_{c2}(\omega)H_{rt2}(\omega) + H_{c3}(\omega)H_{rt3}(\omega) = \frac{1}{1 + \max_{\omega}\{|H_{rt2}(\omega)|^{m} + |H_{rt3}(\omega)|^{m}\}/ N\{|H_{rt2}(\omega)|^{m} + |H_{rt3}(\omega)|^{m}\}} \quad (26)$$

An example of $|H_c(\omega)|$ for m=2 and N=10 is given as 1105 in FIG. 11*b*. We note that $H_c(\omega)$ covers a frequency range from 0.8–7.5 MHz which gives a relative receive bandwidth of 160%. This wide receive bandwidth can then through further filtering be split into a $1^{st}$, $2^{nd}$, $3^{rd}$ and $4^{th}$ harmonic component of the transmitted frequency band. We should emphasize that the exact frequency values can be manipulated through proportional changes in the layer thicknesses both in the high impedance and the matching sections.

In a manufacturing situation, one typically sees a variation of both $H_{rt2}(\omega)$ and $H_{rt3}(\omega)$ between units, which gives problems for using fixed filters $H_{c2}(\omega)$ and $H_{c3}(\omega)$ with different production units of the transducers. A solution to this problem is to digitally store $H_{c2}(\omega)$and $H_{c3}(\omega)$ adapted to the individual $H_{rt2}(\omega)$ and $H_{rt3}(\omega)$ of a particular production unit, for example in an EPROM attached to the particular transducer unit, for example in the transducer instrument connector. Equivalently, one can store the filter impulse responses $h_{c2}(\tau)$ and $h_{c3}(\tau)$ which are the inverse Fourier transforms of $H_{c2}(\omega)$ and $H_{c3}(\omega)$. With arrays, one can also store individual filter responses for each transducer element, or groups of transducer elements, to compensate for variations of the transfer functions between the individual elements.

Figure 13A:
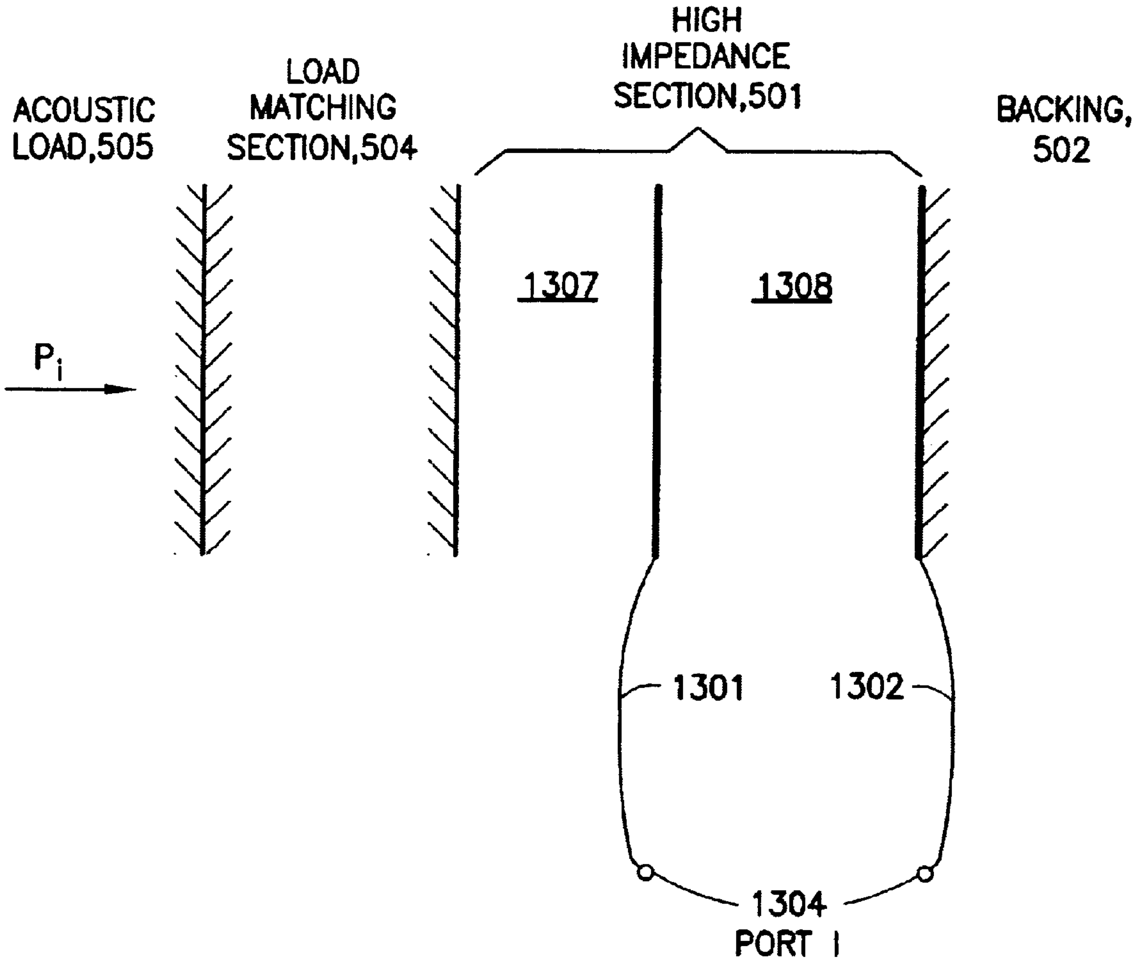
FIG. 13*a* shows a cross section of the transducer.
Figure 13B:
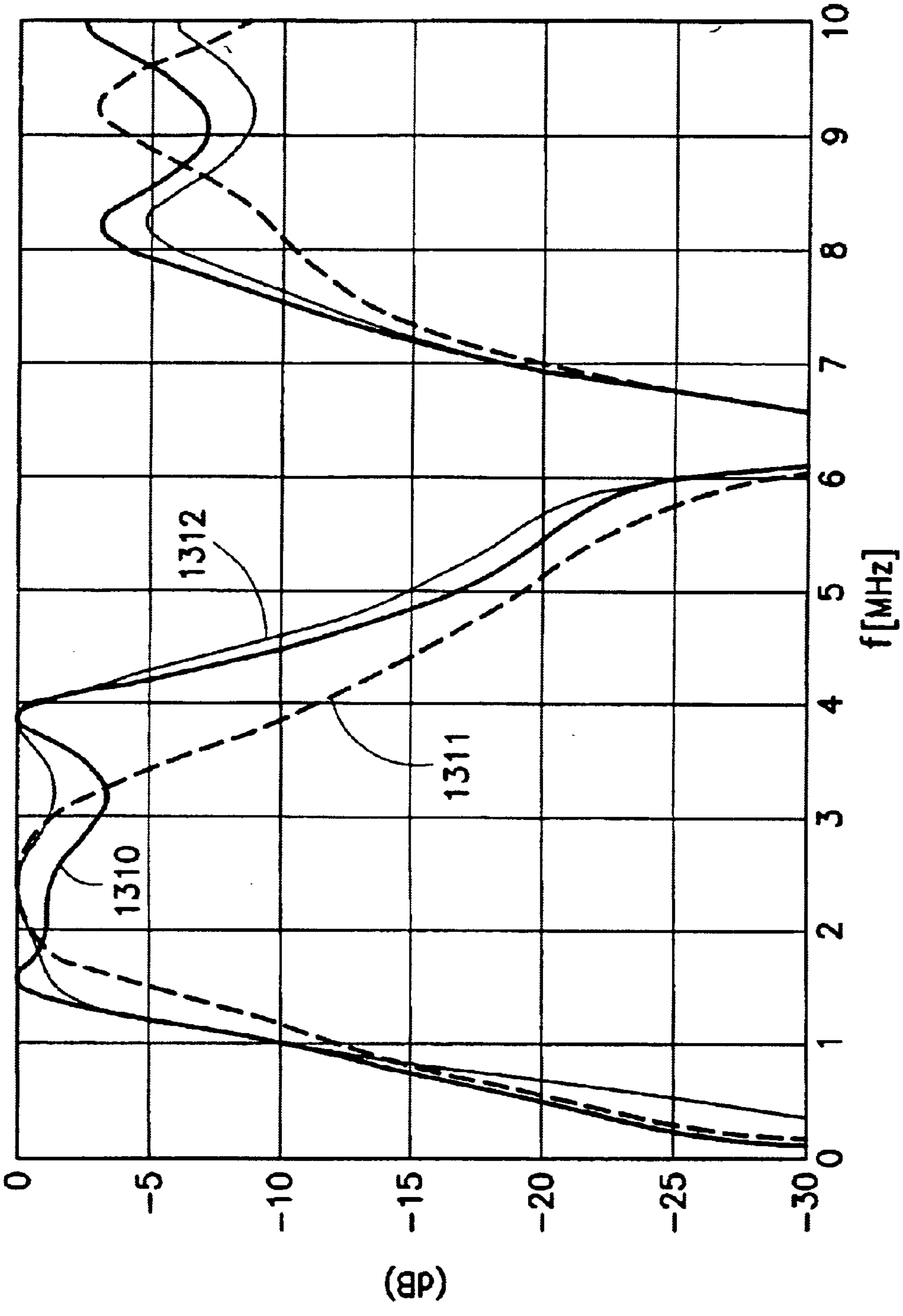
FIG. 13*b* shows both transmit and receive transfer functions of the transducer.

A reduced design with a single electric port according to the invention, is shown in FIG. 13*a*. In this Figure, the high impedance section contains a single piezoelectric layer 1308 with a front elastic layer 1307 with similar characteristic impedance $Z_x$~17MRayl. The piezoelectric layer faces are covered with electrodes 1301 and 1302 to form an electric port 1304, Port I. The front elastic layer, 1307, is used to increase the effective bandwidth of $|H_{stru}|$. An example of transfer functions for this structure is shown in FIG. 13*b*, where the load matching section is composed of a single matching layer with characteristic impedance 3.2 MRayl. The transmit transfer function $|H_{tt}(\omega)|$ of Port I with layer 1307 in place, is shown as 1310, while 1311 shows $|H_{tt}(\omega)|$ with layer 1307 removed. The receive transfer function $|H_{rt}(\omega)|$ of Port I, 1304, with layer 1307 in place when loading the transducer with a complex tuned load at the band center frequency, is shown as 1312. With 1307 in place the relative bandwidth of the transducer is 112%, while with 1307 removed the relative bandwidth is 78%. Hence, the layer 1307 introduces an increase in absolute bandwidth of 60%.

Figure 14:
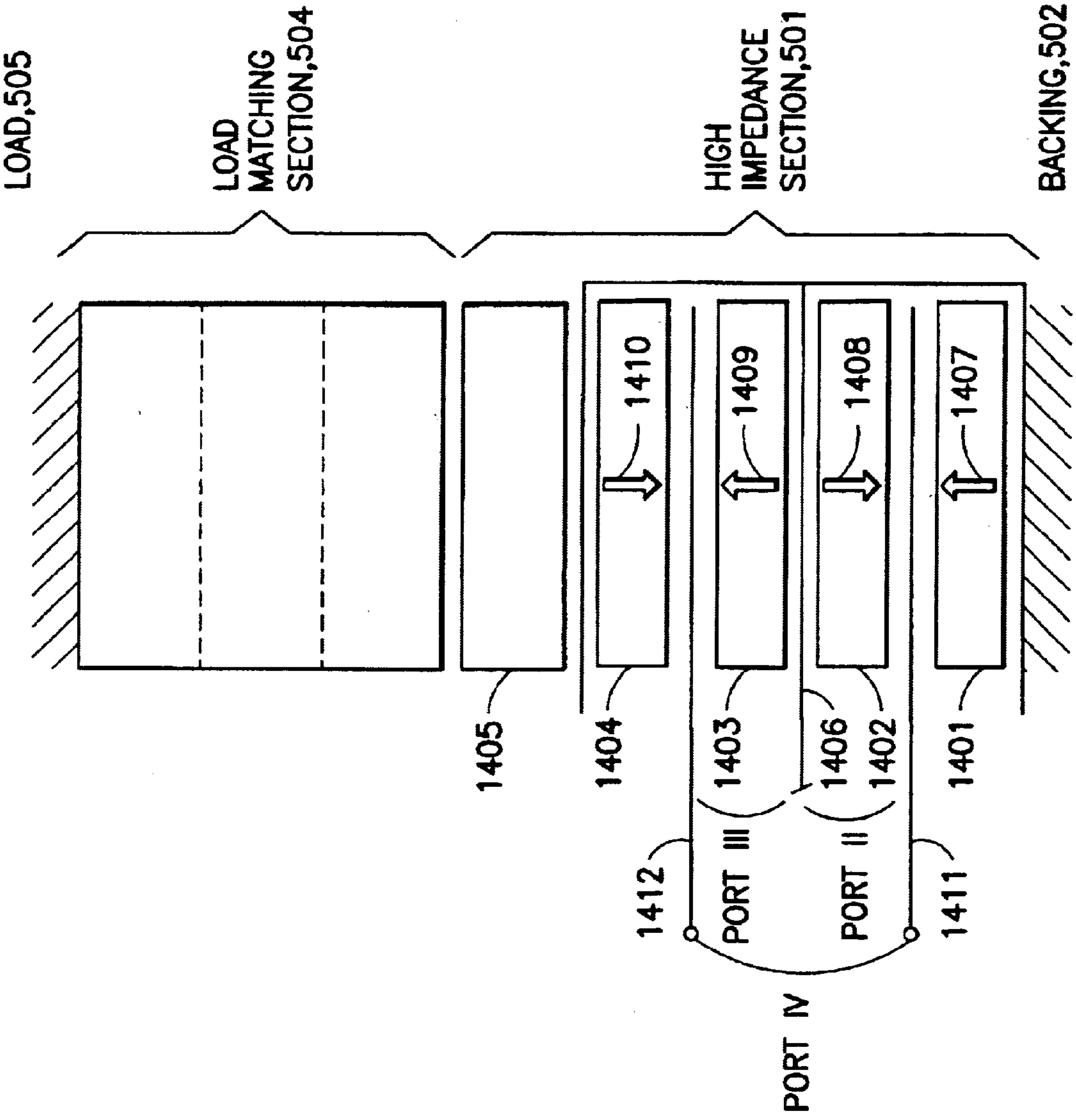
FIG. 14 shows yet another example transducer according to the invention, with multiple electric piezoelectric layer ports that are galvanically combined to electric resultant ports.

One should note that according to the spirit of the invention, the high impedance section could be composed of more piezoelectric layers with electrodes on the surfaces, so that more electrical ports are obtained with different transfer functions. These electric ports could be galvanically combined by serial or parallel coupling to resultant ports, as illustrated by an example in FIG. 14 which shows a high impedance section 501 composed of 4 piezoelectric layers 1401–1404 and an elastic layer 1405 which conveniently could be an Al layer that connects with the common ground electrode 1406. The polarizations of the piezoelectric layers are given by the arrows 1407–1410. The electrodes 1411 and 1412 constitutes together with the ground electrode 1406 the previous Port II and Port III of FIG. 8. These resultant ports could then be electronically steered and coupled together to composite ports as in FIGS. 8*d* and 12*a*.

The Figures illustrate single transducer elements, where it is clear that one can group together many such elements into arrays where the elements are arranged to a two-dimensional radiating surface for example as a linear one- or two-dimensional array, or an annular array. The array surfaces can also be curved according to well-known methods.

For arrays it is then advantageous to use a design where the middle electrode is grounded, as one can then use a single ground plane electrode for the whole array which can be connected to ground at a single or limited number of points. This is especially advantageous with two-dimensional arrays as the active electrodes must have individual connection for each element. The grounding of the middle electrode makes the simplest possible connection to this electrode, and the active front and back electrodes can conveniently be connected through the load matching layers and the backing material.

As an additive feature of the design to improve immunity to interference from external electromagnetic sources, it is advantageous to encapsulate the whole transducer assembly into a thin metal layer that is grounded. The load matching and backing sections can then be used for electric isolation between this encapsulating metal layer, and the active electrodes. With conducting material in the front elastic layer 807/1307/1405, this layer could be grounded and used as part of the electric shielding. With the design in FIG. 14 we note that the ground electrode encompasses the other electrodes and the piezoelectric layers, a solution that increases the resistance to interference from external electromagnetic sources.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, the presented transfer functions are calculated with a selected set of material characteristics and layer thicknesses, and adjustments and improvements in the transfer function characteristics can be obtained by adjustments of the parameters such as the layer thicknesses and characteristic impedances. One hence see that the transducer structures of FIGS. 5, 8, 12, 13, and 14 provide wideband and multiband operations in both transmit and receive modes, according to the general principle of the invention.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An ultrasound bulk wave transducer for transmission and reception of ultrasound pulses in one of a wide band and multiple bands of frequencies, where the ultrasound is radiated from a front face of the transducer and in a thickness direction normal to the radiating front face, comprising:

a high impedance section composed of multiple, stacked layers with at least one piezoelectric layer and at least one additional elastic layer, the at least one piezoelectric layer having a front face and a back face that are covered with conducting electrodes to form two connections for at least one electric layer port, the layers having characteristic impedances so close to each other that the total thickness of the high impedance section defines the thickness resonance frequencies of the high impedance section with open electric ports of the piezoelectric layers, a back face of the high impedance section being acoustically connected to a backing material and optionally through a back impedance matching section comprised of a stack of at least one elastic layer, the backing material having a sufficiently large acoustic absorption that reflected waves in the backing material can be neglected, a front face of the high impedance section being acoustically connected to a load material through a load matching section composed of a set of elastic layers, the characteristic impedance of the layers of the load matching section lying between that of the high impedance section and of the load material with monotonously falling values from the high impedance section towards the load material, and at least one electric layer port being used for electro-acoustic coupling to vibrations of the transducer radiating front face at frequencies at which the thickness of the high impedance section is substantially larger than half a wave length.

2. An ultrasound transducer according to claim 1, wherein the piezoelectric layers are based on a composite of a whole piezoelectric material and a polymer.

3. An ultrasound transducer according to claim 1, wherein at least one additional elastic layer of the high impedance section is an electrically unloaded piezoelectric layer.

4. An ultrasound transducer according to claim 1, wherein at least one additional elastic layer of the high impedance section is made of silicon.

5. An ultrasound transducer according to claim 1, wherein at least one additional elastic layer of the high impedance section is made of a glass or a glass composite.

6. An ultrasound transducer according to claim 1, wherein at least one additional elastic layer of the high impedance section is made of one of alloys and pure forms of one of tin, cadmium, beryllium, lead, bismuth, aluminum, and magnesium.

7. An ultrasound transducer according to claim 1, wherein at least one additional elastic layer of the high impedance section is electrically conducting and also functions as an electrode.

8. An ultrasound transducer according to claim 4 or 7, wherein at least one additional elastic layer of the high impedance section is highly doped silicon.

9. An ultrasound transducer according to claim 1, wherein at least one additional elastic layer of the high impedance section is made of a material with characteristic impedance close to that of the whole piezoelectric material, and the elastic layer is adhered to the whole piezoelectric material before dicing to form the piezoelectric/polymer composite, and the elastic layer is diced together with the piezoelectric layer to manufacture a composite of polymer and the piezoelectric/elastic layers with characteristic impedances close to each other.

10. An ultrasound transducer according to claim 1, wherein first a piezoelectric/polymer composite is made with a coarse distance between the dicing grooves, followed by application of at least one additional elastic layer on the piezoelectric/polymer material, followed by a final dicing of the layered elastic and piezoelectric/polymer structure with dicing grooves between the first dicing grooves, so that uneven relative volume fill of the piezoelectric/polymer and the elastic material/polymer is obtained, for matching the characteristic impedances of the piezoelectric/polymer and the elastic material/polymer composite layers to each other.

11. An ultrasound transducer according to claim 9 or 10, wherein at least one elastic layer is made of a conducting material that functions as electrodes connecting to piezoelectric posts.

12. An ultrasound transducer according to claim 9 or 10, wherein at least one elastic layer is deployed by electroplating onto a metallic layer on the piezoelectric layer before final dicing.

13. An ultrasound transducer according to claim 9 or 10, wherein at least one elastic layer is deployed by thick film printing onto the piezoelectric layer before final dicing.

14. An ultrasound transducer according to claim 9 or 10, wherein a final thickness of the elastic layer is obtained through etching.

15. An ultrasound transducer according to claim 9 or 10, wherein the added elastic layer can be etched, and the relative thickness of the posts of elastic and piezoelectric layers are reduced by etching after final dicing, for tuning of the relative magnitudes of the characteristic impedances of the elastic and piezoelectric layers.

16. An ultrasound transducer according to claim 9 or 10, wherein the added elastic layer can be electroplated, and the relative thickness of the posts of elastic and piezoelectric layers are increased by electroplating after final dicing, for tuning of the relative magnitudes of the characteristic impedances of the elastic and piezoelectric layers.

17. An ultrasound transducer according to claim 9 or 10, wherein tuning of the thickness of the posts of at least one of the elastic and piezoelectric layers are done by additional dicing, for tuning of the relative magnitudes of the characteristic impedances of the elastic and piezoelectric layers.

18. An ultrasound transducer according to claim 9 or 10, wherein at least one elastic layer is made of one of alloys or pure materials of one of gold, iron, copper, silver, brass, cast iron, zirconium, zinc, titanium, germanium, gallium arsenide, tin, cadmium, beryllium, lead, bismuth, silicon, and aluminum.

19. An ultrasound transducer according to claim 9 or 10, wherein at least one of the load and back matching layers are adhered to the layers of the high impedance section before final dicing, followed by final dicing of all of the layers together, filling of the dice grooves with polymer material to form composites with polymer material to obtain piezoelectric/polymer, high impedance elastic/polymer, and impedance matching layer/polymer composites, optionally with different volume fills, so that the characteristic impedances of the said layers are tuned to transfer function requirements.

20. An ultrasound transducer according to claim 19, wherein the added elastic layer, and the load or back matching layers before dicing are made of a conducting material, and wherein a thin metal layer on top of the composite binds conducting posts together to form electrodes for the piezoelectric layers.

21. An ultrasound transducer according to claim 20, wherein the conducting material of the load and back matching layers is made of one of alloys and pure material of one of titanium, germanium, gallium arsenide, tin, cadmium, beryllium, lead, bismuth, silicon, aluminum, and magnesium.

22. An ultrasound transducer according to claim 19, wherein the added matching layers can be etched, and the relative thickness of posts of the matching, high impedance elastic and piezoelectric layers are reduced by etching after the final dicing, for tuning of the relative magnitudes of the characteristic impedances of the said layers to the transfer function requirements.

23. An ultrasound transducer according to claim 19, wherein the added matching layers can be electroplated, and the relative thickness of posts of the matching, high impedance elastic and piezoelectric layers are increased by electroplating after the dicing, for tuning of the relative magnitudes of the characteristic impedances of said layers to the transfer function requirements.

24. An ultrasound transducer according to claim 19, wherein tuning of the thickness of posts of one of the matching, high impedance elastic layers and the piezoelectric layers are done by additional dicing, for tuning of the relative magnitudes of the characteristic impedances of said layers to the transfer function requirements.

25. An ultrasound transducer according to claim 1, wherein at least one of the load and back matching layers are made of one of a glass and a glass/solid particle composite.

26. An ultrasound transducer according to claim 1, wherein at least one of the load or back matching layers are made of a composite of solid particles and a polymer material.

27. An ultrasound transducer according to claim 1, wherein at least one of the load or back matching layers are made of one of alloys and pure materials of one of silicon, aluminum, and magnesium.

28. An ultrasound transducer according to claim 1, wherein the front layer of the back impedance matching section is electrically conducting and in electrical contact with the back piezoelectric layer so that it functions as the back electrode of the back piezoelectric layer.

29. An ultrasound transducer according to claim 28, wherein the front layer of the back matching section is made of one of alloys and pure material of one of bismuth, lead, beryllium, cadmium, tin, gallium arsenide, germanium, titanium, zinc, zirconium, silver, copper, gold, platinum, and tungsten.

30. An ultrasound transducer according to claim 1, wherein the high impedance section is composed of more than one piezoelectric layer covered with electrodes to form multiple electric layer ports for electro-acoustic coupling into a load material in different frequency bands.

31. An ultrasound transducer according to claim 30, wherein electric layer ports are combined into electric resultant ports through direct galvanic connection of the electrodes of the layer ports that are combined to produce one of serial, anti-serial, parallel, and anti-parallel couplings of the layer ports, determined by a polarization direction of the piezoelectric layers and the connection of the electrodes.

32. An ultrasound transducer according to claim 31, wherein the electric resultant ports are more than one, and at least one of the resultant ports provides effective transduction bands at frequencies at which the thickness of the high impedance section is substantially larger than half a wave length.

33. An ultrasound transducer according to claim 30 or 32, wherein active electric ports are combined through electric connection of the electrodes through electronically controllable switches, for electronic selection of electrical combination of the active ports to produce one of serial, anti-serial, parallel, and anti-parallel couplings of the layer ports.

34. An ultrasound transducer according to claim 33, wherein the number of active electric ports is two, defined as a front port closest to the acoustic load and a back port closest to the backing, wherein the back port provides efficient electro-acoustic transduction at frequencies at which the thickness of the high impedance section is substantially larger than half a wave length so that the back port is efficient in a high frequency band, and wherein a low frequency electric port is obtained by electrical serial or electrical parallel coupling of the front and the back ports.

35. An ultrasound transducer according to claim 34, wherein electrical serial coupling of the front and the back ports is obtained with the same polarization directions of the front and the back piezoelectric layers, and wherein a signal is connected between the front electrode of the front port and the back electrode of the back port.

36. An ultrasound transducer according to claim 34, wherein electrical parallel coupling of the front and back ports is obtained with opposite polarization directions of the front and the back piezoelectric layers, and electric connections between the front electrode of the front port and the back electrode of the back port, and middle electrodes of the front port and the back port, and the signal is connected between the front and back electrodes and the middle electrodes of the front and the back ports.

37. An ultrasound transducer according to claim 34, wherein the two active ports are electrically one of anti-parallel and anti-serial combined to form a high frequency electric port.

38. An ultrasound transducer array composed of a plurality of element transducers according to claim 1, said plural transducers being placed by side so that the element front faces form an optionally curved composite array radiating surface, and the electric ports of each element being connected to individual electronic transceiver systems, for electronic steering of array focus and optionally of beam direction.

39. An ultrasound transducer array according to claim 38, wherein at least one of the electrodes internally within the high impedance section is grounded and forms a continuous electrode between all of the plural element transducers throughout the array, for simplified ground connection to the at least one electrode for the whole array, and wherein the other electrodes of the ports connect through one of the front and back faces of the high impedance section and through sides of the high impedance section.

40. A two-dimensional ultrasound transducer array according to claim 39, wherein some of the front electrodes of the front electric ports connect to an instrument through the front elastic layer of the high impedance section, and optionally also through at least one layer of the load matching section, and some of the back electrodes of the back electric ports connect to the instrument through at least one optional back matching layer and optionally through the backing material, while the internal ground electrode extends continuously throughout the whole array.

41. An ultrasound transducer array according to claim 38 and that is encapsulated in a grounded, electrically conducting cage, electrically isolated from the signal electrodes of the transducer array.

42. An ultrasound transceiver system, comprising:

an ultrasound bulk wave transducer with several electric ports coupling to a common acoustic front face port to define electro-acoustic ports, the transfer functions of the electro-acoustic ports having efficient operation in different frequency bands, receive amplifiers selectively connected in receive mode to each electric port to provide receive signals with the transfer functions of the actual electro-acoustic ports, and transmit amplifiers selectively connected to each electric port so that one in transmit mode can select the transmit signal on a selected electro-acoustic port for efficient transmission of ultrasound waves in a frequency band of the selected port, and so that one through selection of combined transmitter signals on at least two electric ports is able to obtain transfer functions of combined electro-acoustic ports combined as one of electric parallel, anti parallel, serial and anti-serial couplings of the ports, and so that one through selection of combined transmitter signals on at least two electric ports is operable to transmit composite signals with components in multiple frequency bands.

43. An ultrasound transceiver system according to claim 42, further comprising an additive signal combination unit that in receive mode combines the received signal from several electro-acoustic ports after the receiver amplifiers, optionally after filtering of signals, to provide receive signals in wide band or multiple frequency bands.

44. An ultrasound transceiver system according to claim 43, wherein the signal combination unit contains filters that provide multiple signals that have a harmonic frequency relation to each other, said frequency relation comprising frequency components in bands with one of a $1^{st}$, a $2^{nd}$, a $3^{rd}$, and a $4^{th}$ harmonic relation to each other.

45. An ultrasound transceiver system according to claim 42, wherein the transducer is formed of several layered sections and wherein ultrasound is radiated from a front face and in the thickness direction normal to the radiating front face, further comprising:

a high impedance section comprised of multiple, stacked layers with characteristic impedances so close to each other that the section functions acoustically as a unit so that a total thickness of the high impedance section defines thickness resonance frequencies of the high impedance section with open electric ports, a back face of the high impedance section being acoustically connected to a backing material, optionally through a back impedance matching section, the backing material having sufficiently large acoustic absorption so that reflected waves in the backing material can be neglected, a front face of the high impedance section being acoustically connected to a load material through a load matching section comprised of a set of elastic layers, the high impedance section being comprised of at least two piezoelectric layers with a front and a back face that are covered with conducting electrodes to form two connections of electric layer ports for each layer, the electric layer ports being such that some of the ports perform efficient electro-acoustic coupling at frequencies at which the thickness of the high impedance section is substantially larger than half a wave length, and other port transfer functions are efficient at frequencies at which the thickness of the high impedance section is below half a wave length with a back impedance lower than a characteristic impedance of the high impedance section and below a quarter wave length with a back impedance higher than the characteristic impedance of the high impedance section.

46. An ultrasound transceiver system according to claim 45, wherein:

the electrodes from some electric layer ports are combined galvanically to form electric resultant ports in one of a series, parallel, anti-parallel and anti-series coupling of the involved layer ports, the transfer functions of the electro-acoustic resultant ports having efficient operation in different frequency bands where at least one of the resultant port transfer functions is efficient at frequencies at which the thickness of the high impedance section is substantially larger than half a wave length, and at least one port transfer function is efficient at frequencies where the thickness of the high impedance section is below half a wave length with a back impedance lower than the characteristic impedance of the high impedance section and below a quarter wave length with a back impedance higher than the characteristic impedance of the high impedance section.

47. An ultrasound transceiver system according to claim 42, including a transducer in accordance with claim 1.

48. An ultrasound transceiver system according to one of claims 42 to 46, wherein the number of electric ports is two and defined as a front port closest to the load and a back port closest to the backing, and electrical polarization of the piezoelectric layers is arranged so that transmit operation in a low frequency band through parallel coupling of the ports is obtained by driving the ports with the same voltage signal where the voltage polarity on each port is referred to the polarization direction of piezoelectric material of the each port, transmit operation in a high frequency band through anti-parallel coupling of the ports is obtained by driving the ports with voltage signals of opposite polarity and the same form where the voltage polarity on each port is referred to the polarization direction of piezoelectric material of the each port, transmit operation in a widest frequency band is obtained through a voltage drive signal at the back port with no drive signal on the front port, transmit operation of combined signals with a combined low and high frequency band is obtained by driving the ports with voltage signals which are the sums of a low frequency signal that is equal on each port and one of a high frequency signal at one port only and high frequency signals that have opposite polarity on each port where the voltage polarity on each port is referred to the polarization direction of piezoelectric material of the each port.

49. An ultrasound array transceiver system, comprising a plurality of ultrasound tranceiver systems according to one of claims 42 to 46, and comprising ultrasound element transducers with multiple electric ports, the element transducers being placed side-by-side so that the element radiating front faces form an optionally curved composite array radiating surface, the electric ports of each element transducer being connected to individual electronic transceivers, for electronic steering of array focus and optionally of beam direction.

50. An ultrasound array transceiver system according to claim 49, wherein at least one of the electrodes internally within the high impedance section of the element transducers is grounded and the grounded electrode forms a continuous electrode between all of the element transducers throughout the array, for simplified connection of the at least one electrode to ground for the whole array.

51. An ultrasound array transceiver system according to claim 50, wherein each element transducer contains two electric ports sharing one common ground electrode situated internally within the high impedance section and extending throughout the array, and the other two electrodes of the ports connect through one of the front and back faces, and sides, of the high impedance section.

52. An ultrasound array transceiver system according to claim 50 or 51, wherein some of the front electrodes of the front electric ports connect to an instrument through an optionally elastic front layer of the high impedance section, and optionally also through at least one load matching layer, and wherein some of the back electrodes of the back electric ports connect to the instrument through one of at least one back matching layer and the backing material, and an internal ground electrode extends continuously throughout the whole array.

53. An ultrasound transducer according to claim 1 and that is encapsulated in a grounded, electrically conducting cage, electrically isolated from signal electrodes of the transducer.

* * * * *